(12) United States Patent
Zhao et al.

(10) Patent No.: US 7,105,812 B2
(45) Date of Patent: *Sep. 12, 2006

(54) MICROFLUIDIC CHIP WITH ENHANCED TIP FOR STABLE ELECTROSPRAY IONIZATION

(75) Inventors: Mingqi Zhao, San Jose, CA (US); Iuliu Blaga, Fremont, CA (US); Luc Bousse, Los Altos, CA (US); John Stults, Redwood City, CA (US); Jing Ni, Sunnyvale, CA (US)

(73) Assignee: Predicant Biosciences, Inc., South San Francisco, CA (US)

( * ) Notice: Subject to any disclaimer, the term of this patent is extended or adjusted under 35 U.S.C. 154(b) by 198 days.

This patent is subject to a terminal disclaimer.

(21) Appl. No.: 10/871,498

(22) Filed: Jun. 18, 2004

(65) Prior Publication Data

US 2005/0047969 A1    Mar. 3, 2005

Related U.S. Application Data

(63) Continuation-in-part of application No. 10/649,350, filed on Aug. 26, 2003, now Pat. No. 6,803,568.

(51) Int. Cl.
*H01J 49/04* (2006.01)
*B01D 59/44* (2006.01)

(52) U.S. Cl. ............... 250/288; 250/281; 250/285; 250/428; 422/100

(58) Field of Classification Search ............... 250/288, 250/282, 281, 285, 428; 422/100
See application file for complete search history.

(56) References Cited

U.S. PATENT DOCUMENTS 4,443,319 A    4/1984    Chait et al.
4,483,885 A    11/1984   Chait et al.
4,908,112 A    3/1990    Pace
4,963,736 A    10/1990   Douglas et al.
5,115,131 A    5/1992    Jorgenson et al.
5,223,226 A    6/1993    Wittmer et al.
5,296,114 A    3/1994    Manz (Continued)

FOREIGN PATENT DOCUMENTS

EP    0653631 B1    11/1994

(Continued)

OTHER PUBLICATIONS

Barnidge, David R. et al., "A design for low-flow sheathless electrospray emitters". *Anal. Chem.* (1999), 71:4115-4118.

(Continued)

*Primary Examiner*—Nikita Wells
(74) *Attorney, Agent, or Firm*—Wilson Sonsini Goodrich & Rosati

(57) ABSTRACT

A microfluidic chip formed with multiple fluid channels terminating at a tapered electrospray ionization tip for mass spectrometric analysis. The fluid channels may be formed onto a channel plate that are in fluid communication with corresponding reservoirs. The electrospray tip can be formed along a defined distal portion of the channel plate that can include a single or multiple tapered surfaces. The fluid channels may terminate at an open-tip region of the electrospray tip. A covering plate may substantially enclose most portions of the fluid channels formed on the channel plate except for the open-tip region. Another aspect of the invention provides methods for conducting mass spectrometric analysis of multiple samples flowing through individual fluid channels in a single microfluidic chip that is formed with a tapered electrospray tip having an open-tip region.

21 Claims, 13 Drawing Sheets

U.S. PATENT DOCUMENTS

| | | | |
|---|---|---|---|
| 5,306,910 A | 4/1994 | Jarrell et al. | |
| RE34,757 E | 10/1994 | Smith et al. | |
| 5,358,618 A | 10/1994 | Ewing et al. | |
| 5,393,975 A | 2/1995 | Hail et al. | |
| 5,423,964 A | 6/1995 | Smith et al. | |
| 5,599,432 A | 2/1997 | Manz et al. | |
| 5,624,539 A | 4/1997 | Ewing et al. | |
| 5,705,813 A | 1/1998 | Appfel et al. | |
| 5,716,825 A | 2/1998 | Hancock et al. | |
| 5,788,166 A | 8/1998 | Valaskovic et al. | |
| 5,800,690 A | 9/1998 | Chow et al. | |
| 5,833,861 A | 11/1998 | Afeyan et al. | |
| 5,856,671 A | 1/1999 | Henion et al. | |
| 5,858,188 A | 1/1999 | Soane et al. | |
| 5,858,195 A | 1/1999 | Ramsey | |
| 5,866,345 A | 2/1999 | Wilding et al. | |
| 5,868,322 A | 2/1999 | Loucks et al. | |
| 5,872,010 A | 2/1999 | Karger et al. | |
| 5,885,470 A | 3/1999 | Parce et al. | |
| 5,914,184 A | 6/1999 | Morman | |
| 5,917,184 A | 6/1999 | Carson et al. | |
| 5,935,401 A | 8/1999 | Amigo | |
| 5,945,678 A | 8/1999 | Yanagisawa | |
| 5,958,202 A | 9/1999 | Regnier et al. | |
| 5,965,001 A | 10/1999 | Chow et al. | |
| 5,969,353 A | 10/1999 | Hsieh | |
| 5,993,633 A | 11/1999 | Smith et al. | |
| 5,994,696 A | 11/1999 | Tai et al. | |
| 6,001,229 A | 12/1999 | Ramsey | |
| 6,010,607 A | 1/2000 | Ramsey | |
| 6,010,608 A | 1/2000 | Ramsey | |
| 6,012,902 A | 1/2000 | Parce | |
| 6,033,546 A | 3/2000 | Ramsey | |
| 6,033,628 A | 3/2000 | Kaltenbach et al. | |
| 6,054,034 A | 4/2000 | Soane et al. | |
| 6,056,860 A | 5/2000 | Amigo et al. | |
| 6,068,749 A | 5/2000 | Karger et al. | |
| 6,086,243 A | 7/2000 | Paul et al. | |
| 6,110,343 A | 8/2000 | Ramsey et al. | |
| 6,123,798 A | 9/2000 | Gandhi et al. | |
| 6,136,212 A | 10/2000 | Mastrangelo et al. | |
| 6,139,734 A | 10/2000 | Settlage et al. | |
| 6,149,870 A | 11/2000 | Parce et al. | |
| 6,156,181 A | 12/2000 | Parce et al. | |
| 6,159,739 A | 12/2000 | Weigl et al. | |
| 6,176,962 B1 | 1/2001 | Soane et al. | |
| 6,187,190 B1 | 2/2001 | Smith et al. | |
| 6,231,737 B1 | 5/2001 | Ramsey et al. | |
| 6,238,538 B1 | 5/2001 | Parce et al. | |
| 6,240,790 B1 | 6/2001 | Swedberg et al. | |
| 6,245,227 B1 | 6/2001 | Moon et al. | |
| 6,277,641 B1 | 8/2001 | Yager | |
| 6,280,589 B1 | 8/2001 | Manz et al. | |
| 6,284,113 B1 | 9/2001 | Bjornson et al. | |
| 6,284,115 B1 | 9/2001 | Apffel | |
| 6,318,970 B1 | 11/2001 | Backhouse | |
| 6,322,682 B1 | 11/2001 | Arvidsson et al. | |
| 6,337,740 B1 | 1/2002 | Parce | |
| 6,342,142 B1 | 1/2002 | Ramsey | |
| 6,368,562 B1 | 4/2002 | Yao | |
| 6,375,817 B1 | 4/2002 | Taylor et al. | |
| 6,394,942 B1 | 5/2002 | Moon et al. | |
| 6,409,900 B1 | 6/2002 | Parce et al. | |
| 6,413,401 B1 | 7/2002 | Chow et al. | |
| 6,416,642 B1 | 7/2002 | Alajoki et al. | |
| 6,417,510 B1 | 7/2002 | Moon et al. | |
| 6,423,198 B1 | 7/2002 | Manz et al. | |
| 6,432,311 B1 | 8/2002 | Moon et al. | |
| 6,444,461 B1 | 9/2002 | Knapp et al. | |
| 6,450,047 B1 | 9/2002 | Swedberg et al. | |
| 6,450,189 B1 | 9/2002 | Ganan-Calvo | |
| 6,454,924 B1 | 9/2002 | Jedrzejewski et al. | |
| 6,454,938 B1 | 9/2002 | Moon et al. | |
| 6,459,080 B1 | 10/2002 | Yin et al. | |
| 6,461,516 B1 | 10/2002 | Moon et al. | |
| 6,462,337 B1 | 10/2002 | Li et al. | |
| 6,464,866 B1 | 10/2002 | Moon et al. | |
| 6,465,776 B1 * | 10/2002 | Moini et al. | 250/285 |
| 6,475,363 B1 | 11/2002 | Ramsey | |
| 6,475,441 B1 | 11/2002 | Parce et al. | |
| 6,481,648 B1 | 11/2002 | Zimmermann et al. | |
| 6,491,804 B1 | 12/2002 | Manz et al. | |
| 6,495,016 B1 | 12/2002 | Nawracala | |
| 6,500,323 B1 | 12/2002 | Chow et al. | |
| 6,514,399 B1 | 2/2003 | Parce et al. | |
| 6,517,234 B1 | 2/2003 | Kopf-Sill et al. | |
| 6,524,456 B1 | 2/2003 | Ramsey et al. | |
| 6,541,768 B1 | 4/2003 | Andrien, Jr. et al. | |
| 6,555,067 B1 | 4/2003 | Gandhi et al. | |
| 6,569,324 B1 | 5/2003 | Moon et al. | |
| 6,576,896 B1 | 6/2003 | Figeys et al. | |
| 6,596,988 B1 | 7/2003 | Corso et al. | |
| 6,602,472 B1 | 8/2003 | Zimmermann et al. | |
| 6,605,472 B1 | 8/2003 | Skinner et al. | |
| 6,607,644 B1 | 8/2003 | Apffel, Jr. | |
| 6,621,076 B1 | 9/2003 | van de Goor et al. | |
| 6,627,076 B1 | 9/2003 | Griffiths | |
| 6,627,882 B1 | 9/2003 | Schultz et al. | |
| 6,632,655 B1 | 10/2003 | Mehta et al. | |
| 6,653,625 B1 | 11/2003 | Andersson et al. | |
| 6,670,607 B1 | 12/2003 | Wood et al. | |
| 6,681,788 B1 | 1/2004 | Parce et al. | |
| 6,695,009 B1 | 2/2004 | Chien et al. | |
| 6,709,559 B1 | 3/2004 | Sundberg et al. | |
| 6,733,645 B1 | 5/2004 | Chow | |
| 6,744,046 B1 | 6/2004 | Valaskovic et al. | |
| 6,803,568 B1 * | 10/2004 | Bousse et al. | 250/288 |
| 6,814,859 B1 | 11/2004 | Koehler et al. | |
| 6,827,095 B1 | 12/2004 | O'Connor et al. | |
| 2001/0037979 A1 | 11/2001 | Moon et al. | |
| 2001/0041357 A1 | 11/2001 | Fouillet et al. | |
| 2002/0036140 A1 | 3/2002 | Manz et al. | |
| 2002/0041827 A1 | 4/2002 | Yager et al. | |
| 2002/0079219 A1 | 6/2002 | Zhao et al. | |
| 2002/0100714 A1 | 8/2002 | Staats | |
| 2002/0110902 A1 | 8/2002 | Prosser et al. | |
| 2002/0117517 A1 | 8/2002 | Unger et al. | |
| 2002/0121487 A1 | 9/2002 | Robotti et al. | |
| 2002/0122474 A1 | 9/2002 | Zhao et al. | |
| 2002/0123153 A1 | 9/2002 | Moon et al. | |
| 2002/0139931 A1 | 10/2002 | Yin et al. | |
| 2002/0158195 A1 | 10/2002 | Andersson et al. | |
| 2002/1070825 | 11/2002 | Lee et al. | |
| 2002/0182649 A1 | 12/2002 | Weinberger et al. | |
| 2003/0000835 A1 | 1/2003 | Witt et al. | |
| 2003/0017609 A1 | 1/2003 | Yin et al. | |
| 2003/0026740 A1 | 2/2003 | Staats | |
| 2003/0029724 A1 | 2/2003 | Derand et al. | |
| 2003/0047680 A1 | 3/2003 | Figeys et al. | |
| 2003/0066959 A1 | 4/2003 | Andersson et al. | |
| 2003/0073260 A1 | 4/2003 | Corso | |
| 2003/0082080 A1 | 5/2003 | Zimmermann et al. | |
| 2003/0089605 A1 * | 5/2003 | Timperman | 204/450 |
| 2003/0089606 A1 | 5/2003 | Parce et al. | |
| 2003/0106799 A1 | 6/2003 | Covington et al. | |
| 2003/0111599 A1 | 6/2003 | Staats | |
| 2003/0141392 A1 | 7/2003 | Nilsson et al. | |
| 2003/0146757 A1 | 8/2003 | Aguero et al. | |
| 2003/0148922 A1 | 8/2003 | Knapp et al. | |
| 2003/0153007 A1 | 8/2003 | Chen et al. | |
| 2003/0180965 A1 | 9/2003 | Yobas et al. | |
| 2003/0213918 A1 | 11/2003 | Kameoka et al. | |
| 2003/0215855 A1 | 11/2003 | Dubrow et al. | |
| 2003/0224531 A1 | 12/2003 | Brennen et al. | |

| | | | |
|---|---|---|---|
| 2004/0075050 A1 | 4/2004 | Rossier et al. | |
| 2004/0084402 A1 | 5/2004 | Ashmead et al. | |
| 2004/0096960 A1 | 5/2004 | Burd Mehta et al. | |
| 2004/0159783 A1 | 8/2004 | Gavin et al. | |
| 2004/0206399 A1 | 10/2004 | Heller | |
| 2004/0229377 A1 | 11/2004 | Chen et al. | |

FOREIGN PATENT DOCUMENTS

| | | |
|---|---|---|
| GB | 2379554 | 3/2003 |
| WO | WO-91/11015 A1 | 7/1991 |
| WO | WO-96/04547 A1 | 2/1996 |
| WO | WO-96/36425 A1 | 11/1996 |
| WO | WO-00/41214 A1 | 7/2000 |
| WO | WO-00/62039 A1 | 10/2000 |
| WO | WO 01/57263 | 8/2001 |
| WO | WO 01/94907 A2 | 12/2001 |
| WO | WO-02/30486 A2 | 4/2002 |
| WO | WO-02/45865 A1 | 6/2002 |
| WO | WO-02/47913 A1 | 6/2002 |
| WO | WO-02/55990 A2 | 7/2002 |
| WO | WO-02/80222 A1 | 10/2002 |
| WO | WO 03/004160 | 1/2003 |
| WO | WO 03/019172 | 3/2003 |
| WO | WO-03/54488 A1 | 7/2003 |
| WO | WO 2004/044574 A1 | 5/2004 |
| WO | WO 2004/051697 | 6/2004 |
| WO | WO 2004/062801 A1 | 7/2004 |
| WO | WO 2004/067162 A2 | 8/2004 |
| WO | WO 2004/070051 A2 | 8/2004 |

OTHER PUBLICATIONS

Lion, Niels et al., "Flow-rate characterization of microfabricated polymer microspray emitters". *Rapid Communications in Mass Spectrometry* (2004), 18:1614-1620.

Nilsson, Stefan et al., "A simple and robust conductive graphite coating for sheathless electrospray emitters used in capillary electrophoresis/mass spectrometry". *Rapid Communications in Mass Spectrometry* (2001), 15:1997-2000.

Rossier, Joel S. et al., "Thin-chip microspray system for high-performance fourier-transform ion-cyclotron resonance mass spectrometry of biopolymers". *Agew. Chem. Int. Ed.* (2003), 42:53-58.

Wetterhall, Magnus et al., "A conductive polymeric material used for nanospray needle and low-flow sheathless electrospray ionization applications", *Anal. Chem.* (2002), 74:239-245.

Yarin, A.L. et al., "Taylor cone and jetting from liquid droplets in electrospinning of nanofibers", *Journal of Applied Physics* (2001), 90:4836-4846.

Auriola, Seppo et al., "Enhancement of sample loadings for the analysis of oligosaccharides isolated from *Pseudomonas aeruginosa* using transient isotachophoresis—electrospray—mass spectrometry". *Electrophoresis* (1998), 19:2665-2676.

Balaguer, E. et al., "Comparison of sheathless and sheathless and sheath flow electrospray interfaces for on line capillary electrophoresis mass spectrometry of therapeutic peptide hormones". *Diagonal 647*, 08028, (2004), Salzberg, Austria.

Banks, Jr., J. Fred et al., "Detection of fast capillary electrophoresis peptide and protein separations using electrospray ionization with a time-of-flight mass spectrometer". *Anal. Chem.* (May 1, 1996), 68(9):1480-1485.

Banks, J. Fred, "Recent advances in capillary electrophoresis/ electrospray/mass spectrometry". *Electrophoresis* (1997), 18:2255-2266.

Chang, Yan Zin et al., "Sheathless capillary electrophoresis/ electrospray mass spectrometry using a carbon-coated fused-silica capillary".*Anal. Chem.* (Feb. 1, 2000), 72(3):626-630.

Chen, Yet-Ran et al., "A low-flow CE/electrospray ionization MS interface for capillary zone electrophoresis, large-volume sample stacking, and micellar electrokinetic chromatography". *Anal. Chem.* (Feb. 1, 2003), 75(3):503-508.

Chien, Ring-Ling et al., "Sample stacking of an extremely large injection volume in high-performance capillary electrophoresis". *Anal. Chem.* (1992), 64:1046-1050.

Ding, Jianmei et al., "Advances in CE/MS: recent developments in interfaces and applications". *Analytical Chemistry News & Features* (Jun. 1, 1999), 378A-385A.

Figeys, Daniel et al., "High sensitivity analysis of proteins and peptides by capillary electrophoresis-tandem mass spectrometry: recent developments in technology and applications". *Electrophoresis*, (1998), 19:885-892.

Figeys, Daniel et al., "Protein identification by solid phase microextraction-capillary zone electrophoresis-microelectrospray-tandem mass spectrometry". *Nature Biotechnology* (Nov. 1996), 14:1579-1583.

Foret, Frantisek et al., "Trace analysis of proteins by capillary zone electrophoresis with on-column transient isotachophoretic preconcentration". *Electrophoresis* (1993), 14:417-428.

Guo, Xu et al., "Analysis of metallonthioneins by means of capillary electrophoresis coupled to electrospray mass spectrometry with sheathless interfacing" *Rapid Commun. Mass Spectrom*, (1999), 13:500-507.

Janini, George M. et al., "A sheathless nanoflow electrospray interface for on-line capillary electrophoresis mass spectrometry". *Anal. Chem.* (2003), 75:1615-1619.

Johansson, I. Monika et al., "Capillary electrophoresis-atmospheric pressure ionization mass spectrometry for the characterization of peptides". *Journal of chromatography* (1991), 554:311-327.

Kaiser, Thorsten et al., "Capillary electrophoresis coupled to mass spectrometer for automated and robust polypeptide determination in body fluids for clinical use". *Electrophoresis* (2004), 25:2044-2055.

Kaiser, Thorsten et al., "Capillary electrophoresis coupled to mass spectrometry to establish polypeptide patterns in dialysis fluids". *Journal of Chromatography A* (2003) 1013:157-171.

Kelly, John F. et al., "Capillary zone electrophoresis-electrospray mass spectrometry at submicroliter flow rates: practical considerations and analytical performance". *Anal. Chem.* (1997), 69:51-60.

Kirby, Daniel P. et al., "A CE/ESI-MS interface for stable, low-flow operation". *Anal. Chem.* (1996), 68:4451-4457.

Larsson, Marita et al., "Transient isotachophoresis for sensitivity enhancement in capillary electrophoresis-mass spectrometry for peptide analysis". *Electrophoresis* (2000), 21:2859-2865.

Lee, Edgar D. et al., "On-line capillary zone electrophoresis-ion spray tandem mass spectrometry for the determination of dynorphins". *Journal of Chromatography* (1988), 458:313-321.

Moini, Mehdi, "Design and performance of a universal sheathless capillary electrophoresis to mass spectrometry interface using a split-flow technique". *Anal. Chem.* (2001), 73:3497-3501.

Neusub, Christian et al., "A robust approach for the analysis of peptides in the low femtomole range by capillary electrophoresis-tandem mass spectrometry". *Electrophoresis* (2002), 23:3149-3159.

Olivares, Jose A. et al., "On-line mass spectrometric detection for capillary zone electrophoresis". *Anal. Chem.* (1987), 59:1230-1232.

Paroni, Rita et al., "Creatinine determination in serum by capillary electrophoresis". *Electrophoresis* (2004), 25:463-468.

Rohde, E. et al., "Comparison of protein mixtures in aqueous humor by membrane preconcentration—capillary electrophoresis—mass spectrometry". *Electrophoresis* (1998), 19:2361-2370.

Sanz-Nebot, Victoria et al., "Capillary electrophoresis coupled to time of flight-mass spectrometry of therapeutic peptide hormones". *Electrophoresis* (2003), 24:883-891.

Smith, Richard D. et al., "Capillary zone electrophoresis-mass spectrometry using an electrospray ionization interface". *Anal. Chem.* (1988), 60:436-441.

Smith, Richard D. et al., "New developments in biochemical mass spectrometry : electrospray ionization", *Anal. Chem.* (1990), 62:882-899.

Stroink, Thom et al., "On-line coupling of size exclusion and capillary zone electrophoresis via a reversed-phase C18 trapping column for the analysis of structurally related enkephalines in cerebrospinal fluid". *Electrophoresis* (2003), 24:897-903.

Tempels, F.W. Alexander et al., "Chromatographic preconcentration coupled to capillary electrophoresis via an in-line injection valve". *Anal. Chem.* (2004), 76:4432-4436.

Tomlinson, Andy J. et al., "Systematic development of on-line membrane preconcentration-capillary electrophoresis-mass spectrometry for the analysis of peptide mixtures". *Journal of Capillary Electrophoresis* (Sep./Oct. 1995), 2(5):225-233.

Valaskovic, Gary A. et al., "Automated orthogonal control system for electrospray ionization mass spectrometry". ASMS Conference on Mass Spectrometry and Allied Topics held on May 23-27, 2004, *New Objective, Inc.* (2004):1-5, Nashville, TN.

Villanueva, Joseph et al., "Serum peptide profiling by magnetic particle-assisted, automated sample processing and MALDI-TOF mass spectrometry". *Anal. Chem.* (Mar. 15, 2004), 76(6):1560-1570.

Von Brocke, Alexander et al., "Recent advances in capillary electrophoresis/electrospray-mass spectrometry". *Electrophoresis* (2001), 22:1251-1266.

Whitt, Jacob T. et al., "Capillary electrophoresis to mass spectrometry interface using a porous junction". *Anal. Chem.* (May 1, 2003), 75(9):2188-2191.

Wittke, Stefan et al., "Determination of peptides and proteins in human urine with capillary electrophoresis-mass spectrometry, a suitable tool for the establishment of new diagnostic markers". *Journal of Chromatography A* (2003), 1013:173-181.

Zhu, Xiaofeng et al., "A colloidal graphite-coated emitter for sheathless capillary electrophoresis/nanoelectrospray ionization mass spectrometry". *Anal. Chem* . (2002), 74:5405-5409.

Stults et al., U.S. Appl. No. 10/681,742 entitled "Methods and apparatus for self-optimization of electrospray ionization devices", filed Oct. 7, 2003.

Bousse et al., U.S. Appl. No. 10/794,572 entitled "Microfluidic devices and methods", filed Mar. 4, 2004.

Advanced Bioanalytical Services, Inc., "Advanced BioAnalytical Services, Inc. gains patent rights to Novel microfluidic handling system". <<http://www.advion.com/neulicensepressl.html>>. Downloaded on May 9, 2002, 2 pages.

Advion Biosciences, "Automated Nanospray—Employing Advion's ESI chip and automated sample delivery robot". <<http://www.advion.com/advion_auxfiles/AutomatedNanospray/sld001.htm>>. Downloaded May 9, 2002, 13 pages.

Advion Biosciences, "Coming soon . . . the Advion NanoMate 100". <<http://www.advion.com>>. Downloaded May 9, 2002, 6 pages.

Applera Corp., "Applied Biosystems, northeastern UN and Professor Barry L. Karger, Ph.D. collaboration to research advance separation technology for protection". <<http://www.applera.com/press/prccorp111901a.html>>. Downloaded May 9, 2002, 3 pages.

Becker, Holger, et al., "Polymer microfluidic devices". Talanta (2002), 56:267-287.

Bings, Nicolas H., "Microfluidic devices connected to fuse-silica capillaries with minimal dead volume". Anal. Chem. (1999), 71:3292-3296.

Cao, Ping et al., "Analysis of peptides, proteins, protein digests, and whole human blood by capillary electrophoresis/electrospray ionization-mass spectrometry using an in-capillary electrode sheathless interface". J Am Soc Mass Spectrometry (1998), 9:1081-1088.

Chan, Jason H., et al., "Microfabricated polymer devices for automated sample delivery of peptides for analysis by electrospray ionization tandem mass spectrometry". Anal. Chem. (1999), 71:4437-4444.

Chen, Shu-Hui, et al., "A disposable poly(methylmethacrylate)-based microfluidic module for protein identification by nanoelectrospray ionization-tandem mass spectrometry". Electrophoresis (2001) 22:3972-3977.

Chiou, Chi-Han, et al., "Micro devices integrated with microchannels and electrospray nozzles using PDMS casting techniques". Sensors and Actuators (2002), B 4311:1-7.

Deng, Yuzhong, et al., "Chip-based quantitative capillary electrophoresis/mass spectrometry determination of drugs in human plasma". Analytical Chemistry (Apr. 1, 2001), 73(7)1432-1439.

DIAGNOSWISS, Disposable nano-electrospays. <<http://www.diagnoswiss.com/products/disp_nano_electr.html>>. Downloaded May 9, 2002, 2 pages.

Figeys, Daniel, et al., "A microfabricated device for rapid protein identification by microelectrospray ion trap mass spectrometry". Anal. Chem. (1997) 69:3153-3160.

Figeys, Daniel, et al., "Nanoflow solvent gradient delivery from a microfabricated device for protein identification by electrospray ionization mass spectrometry". Anal. Chem. (1998) 70:3721-3727.

Geromanos, S., et al., "InJection adaptable Fine Ionization Source ('JaFIS') for Continuous Flow Nano-electrospray". Rapid Commun. Mass Spectrom (1998) 12:551-556.

Geromanos, S., et al., "Tuning of an electrospray ionization source for maximum peptide-ion transmission into a mass spectrometer". Anal. Chem. (2000) 72(4)777-790.

Gobry, Véronique, et al., "Microfabricated polymer injector for direct mass spectrometry coupling". Proteomics (2002), 2:405-412.

Hayes, Roger N., et al., "Collision-induced dissociation". Methods in Enzymology (1990), 193:237-263.

Issaq, Haleem J., et al., "SELDI-TOF MS for diagnostic proteomics". Analytical Chemistry (Apr. 1, 2003) 149-155.

Jiang, Yun, et al., "Integrated plastic microfluidic devices with ESI-MS for drug screening and residue analysis". Anal. Chem. (2001) 73:2048-2053.

Kameoka, Jun, et al., "An electrospray ionization source for integration with microfluidics". Analytical Chemistry (Nov. 15, 2002), 74:5897-5901.

Kameoka, Jun, et al., "A polymeric microfluidic chip for CE/MS determination of small molecules". Anal. Chem. (2001), 73:1935-1941.

Kim, Jin-Sung, et al., "Microfabricated PDMS multichannel emitter for electrospray ionization mass spectrometry". J. Am. Soc. Mass. Spectrom (2001) 12:453-469.

Kim, Jin-Sung, et al., "Microfabrication of polydimethylsiloxane electrospray ionization emitters". Journal of Chromatography (2001), 924:137-145.

Kim, Jin-Sung, et al., "Miniaturized multichannel electrospray ionization emitters on poly(dimethylsiloxane) microfluidic devices)". Electrophoresis (2001), 22:3993-3999.

Koutny, Lance B., et al., "Microchip electrophoretic immunoassay for serum cortisol". Anal. Chem. (1996) 68:18-22.

Lazar, Iulia M., et al., "Subattomole-sensitivity microchip nanelectropray source with time-of-flight mass spectrometry detection". Anal. Chem. (1999) 71:3627-3631.

Li, Jianjun, et al., "Application of microfluidic devices to proteomics research". Molecular & Cellular Proteomics (2002) 157-168.

Li, Jianjun, et al., "Rapid and sensitive separation of trace level protein digests using microfabricated devices coupled to a quadrupole—time-of-flight mass spectrometer". Electrophoresis (2000) 21:198-210.

Li, Jianjun, et al., "Separation and identification of peptides from gel-isolated membrane proteins using a microfabricated device for combined capillary electrophoresis/nanoelectrospray mass spectrometry". Anal. Chem. (2000) 72:599-609.

Lin, Yuehe, et al., "Microfluidic devices on polymer substrates for bioanalytical applications". Pacific Northwest National Laboratory (1999), Richland, WA, USA, 10 pages.

Liu, Hanghui, et al., "Development of multichannel devices with an array of electrospray tips for high-throughput mass spectrometry". Anal. Chem. (2000) 72:3303-3310.

Neuhoff, Nils V., et al., "Mass spectrometry for the detection of differentially expressed proteins: a comparison of surface-enhanced laser desorption/ionization and capillary electrophoresis/mass spectrometry". Rapid Comm. In Mass Spectrometry (2004), 18:149-156.

Oleschuk, Richard D., et al., "Analytical microdevices for mass spectrometry". Trends in Analytical Chemistry (2000) 19(6):379-388.

Premstaller, Andreas, et al., "High-Performance liquid chromatography—electrospray ionization mass spectrometry using monolithic capillary columns for proteomic studies". Anal. Chem. (2001) 73:2390-2396.

Ramsey, R.S., et al. "Generating electrospray from microchip devices using electroosmotic pumping". Analytical Chemistry (Mar. 15, 1997), 69(6)1174-1178.

Rocklin, Roy D. et al., "A microfabricated fluidic device for performing two-dimensional liquid-phase separations". Anal. Chem. (2000) 72:5244-5249.

Rohner, Tatiana, et al., "Polymer microspray with an integrated thick-Film microelectrode". Analytical Chemistry (Nov. 15, 2001), 73(22)5353-5357.

Schmitt-Kopplin, Philippe, et al., "Capillary electrophoresis—mass spectrometry: 15 years of developments and applications". Electrophoresis (2003), 3837-3867.

Schultz, Gary A., et al., "A fully integrated monolithic microchip electrospray device for mass spectrometry". Anal. Chem. (2000) 72:4058-4063.

Selby, David S., et al., "Direct quantification of alkaloid mixtures by electrospray ionization mass spectrometry". Journal of Mass Spectrometry (1998) 33:1232-1236.

Srinivasan, Thara, "ESI and/or CE on microfluidic chips". Literature review (Sep. 18, 2002) 14 pages.

Svedberg, Malin, et al., "Sheathless electrospray from polymer microchips". Anal. Chem. (2003) 75:3934-3940.

Tang, Keqi, et al., "Generation of multiple electrosprays using microfabricated emitter arrays for improved mass spectrometric sensitivity". Anal. Chem. 2001) 73:1658-1663.

Tang, Ning, et al., "Current developments in SELDI affinity technology". Mass Spectrometry Reviews (2004), 23:34-44.

Tomlinson, Andy J., et al., "Investigation of drug metabolism using capillary electrophoresis with photodiode array detection and on-line mass spectrometry equipped with an array detector". Electrophoresis (1994), 13:62-71.

Tomlinson, Andy J. et al., "Utility of Membrane Preconcentration—Capillary Electrophoresis—Mass Spectrometry in Overcoming Limited Sample Loading for Analysis of Biologically Derived Drug Metabolites, Peptides, and Proteins". J Am Soc Mass Spectrom (1997), 8:15-24.

Wachs, Timothy, et al., "Electrospray device for coupling microscale separations and other miniaturized devices with electrospray mass spectrometry". Anal. Chem. (2001) 73:632-638.

Wang, Michael Z., et al., "Analysis of human serum proteins by liquid phase isoelectric focusing and matrix-assisted laser desorption/ionization-mass spectrometry". Proteomics (2003), 3:1661-1666.

Wen, Jenny, et al, "Microfabricated isoelectric focusing device for direct electrospray ionization-mass spectrometry". Electrophoresis (2000) 21:191-197.

Wright, G.L. et al., "Proteinchip surface enhanced laser desorption/ionization (SELDI) mass spectrometry: a novel protein biochip technology for detection of prostate cancer biomarkers in complex protein mixtures". Prostate Cancer and Prostatic Diseases (1999) 2:264-276.

Xue, Qifeng, et al., "Multichannel microchip electrospray mass spectrometry". Analytical Chemistry (Feb. 1, 1997), 69(3)426-430.

Zhang, et al., "A microdevice with integrated liquid junction for facile peptide and protein analysis by capillary electrophoresis/electrospray mass spectrometry". Anal. Chem. (2000) 72:1015-1022.

Zhang, et al., "Microfabricated devices for capillary electrophoresis-electrospray mass spectrometry". Anal. Chem. (Aug. 1, 1999), 71(5)3258-3264.

CRISP—Computer retrieval of information on scientific projects [abstract], <<http://commons.clt.nlh.gov/crisp3/CRISP_LIB.getdoc?textkey=6388327&p_grant_num=5R01HG002033-03&p_query=&ticket=...>>. Downloaded May 9, 2002, 2 pages.

Czaplewski, David A., et al., "Nanofluidic Channels withi Elliptical Cross Sections", Applied Physics Letters, 83(23), (Dec. 8, 2003), 4836,4838.

Czaplewski, David A., et al., "Nanomechanical Oscillators Fabricated Using Polymeric Nanofiber Templates", Nano Letters, 4 (2004), 437-439.

Czaplewski, David A., et al., "Nonlithographic Approach to Nanostructure Fabrication Using a Scanned Electrospinning Source", Journal of Vacuum Science & Technology B: Microelectronics and Nanometer Structures, 21(6), (Nov. 2003), 2994-2997.

Geracimos, A., "Outwitting Ovarian Cancer". Correlogic Systems, Inc., Press Release dated Apr. 16, 2002, 4 pages.

Kameoka, Jun, et al., "A Scanning Tip Electrospinning Source for Deposition of Oriented Nanofibres", Nanotechnology, 14, (2003), 1124-1129.

Kameoka, Jun, et al., "An Arrow Shaped Silicon Tip for Polymeric Nanofiber Fabrication", Journal of Photopolymer Science and Technology, 16, (2003), 423-426.

Kameoka, Jun, et al., "Fabrication of Oriented Polymeric Nanofibers on Planar Surfaces by Electrospinning", Applied Physics Letters, 83(2), (Jul. 14, 2003), 371-373.

Kameoka, Jun, et al., "Polymeric Nanowire Architecture", Journal of Materials Chemistry, 14, (2004), 1503-1505.

Liu, Haiqing, et al., "Polymeric Nanowire Chemical Sensor", Nano Letters, 4, (2004), 671-675.

Valaskovic, Gary A. et al., "Automated orthogonal control system for electrospray ionization". J Am Soc for Mass Spectrom (2004): 15:1201-1215.

Yuan, Cheng-Hui, et al., "Sequential Electrospray Analysis Using Sharp-Tip Channels Fabricated on a Plastic Chip", Anal. Chem., 73, (2001), 1080-1083.

Bousse, et al., U.S. Appl. No. 10/903,248 entitled "Microfluidic Devices with Electrical Contact for Stable Electrophoresis and Electrospray," filed Jul. 29, 2004.

Bousse, et al., U.S. Appl. No. 11/031,963 entitled "Electrospray Apparatus with an Integrated Electrode," filed Jan. 6, 2005.

* cited by examiner

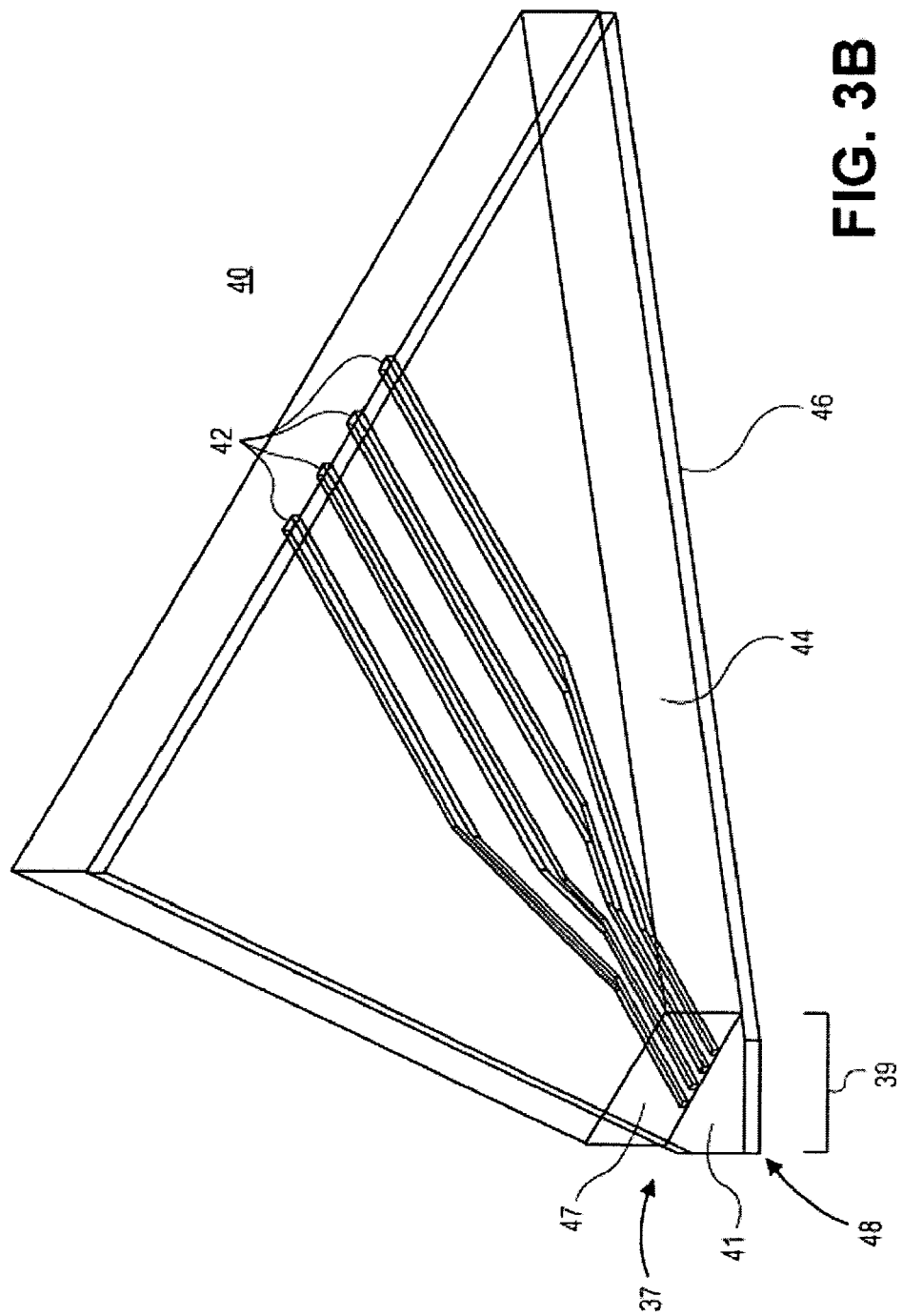

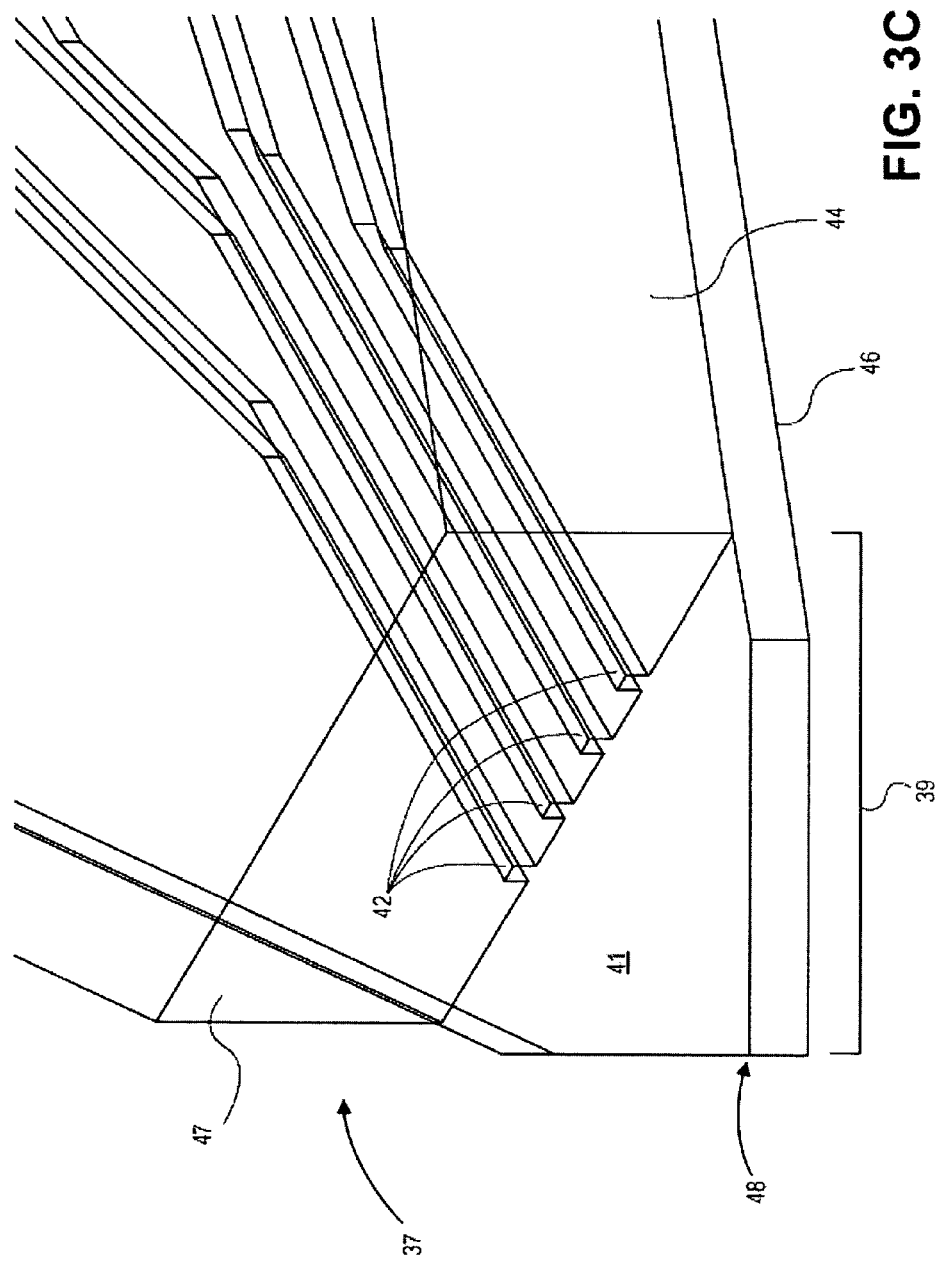

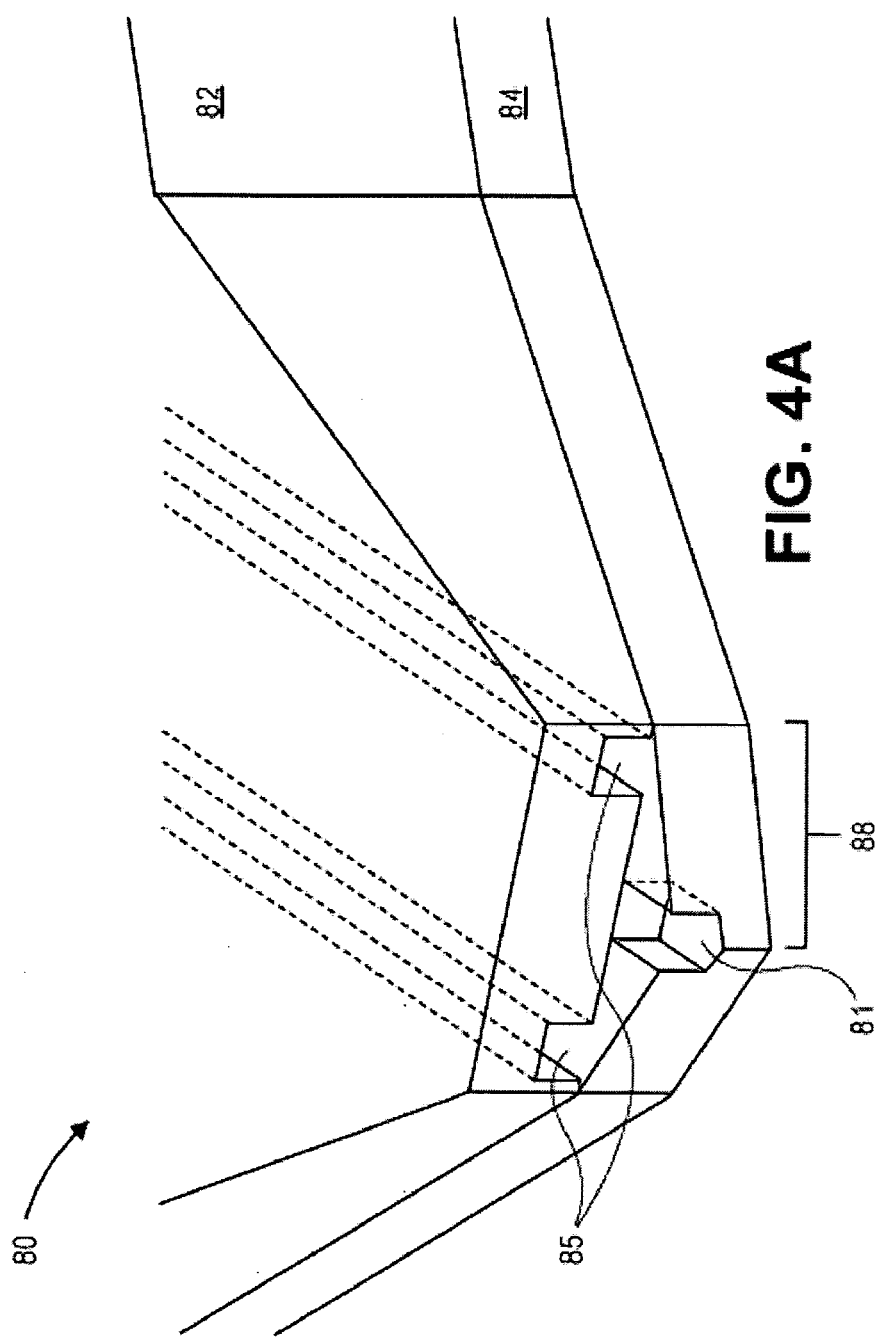

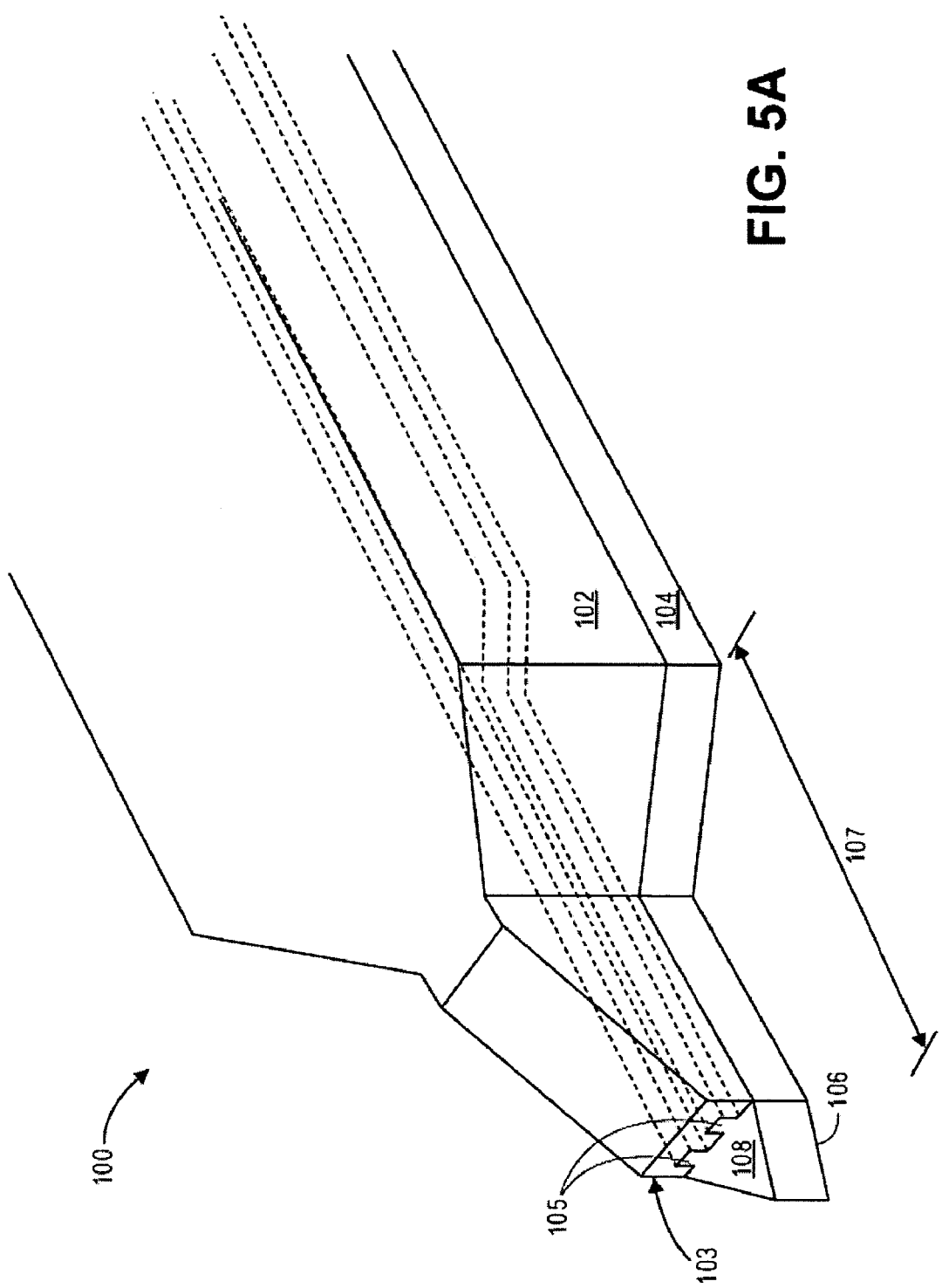

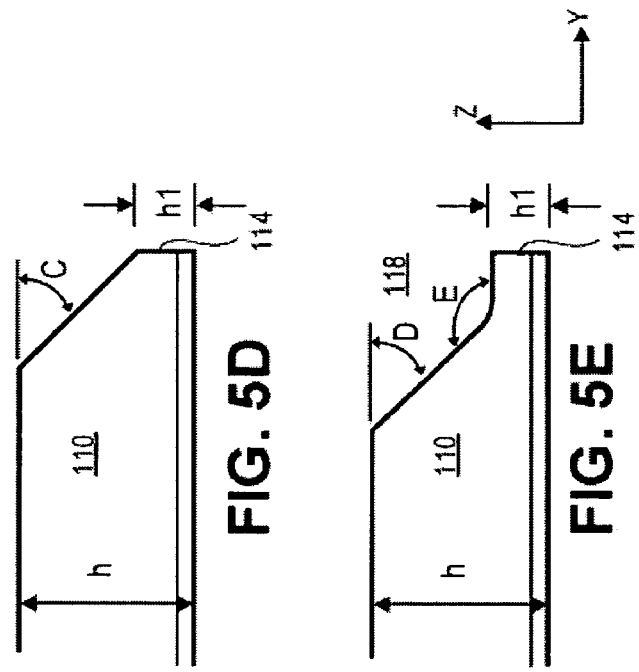
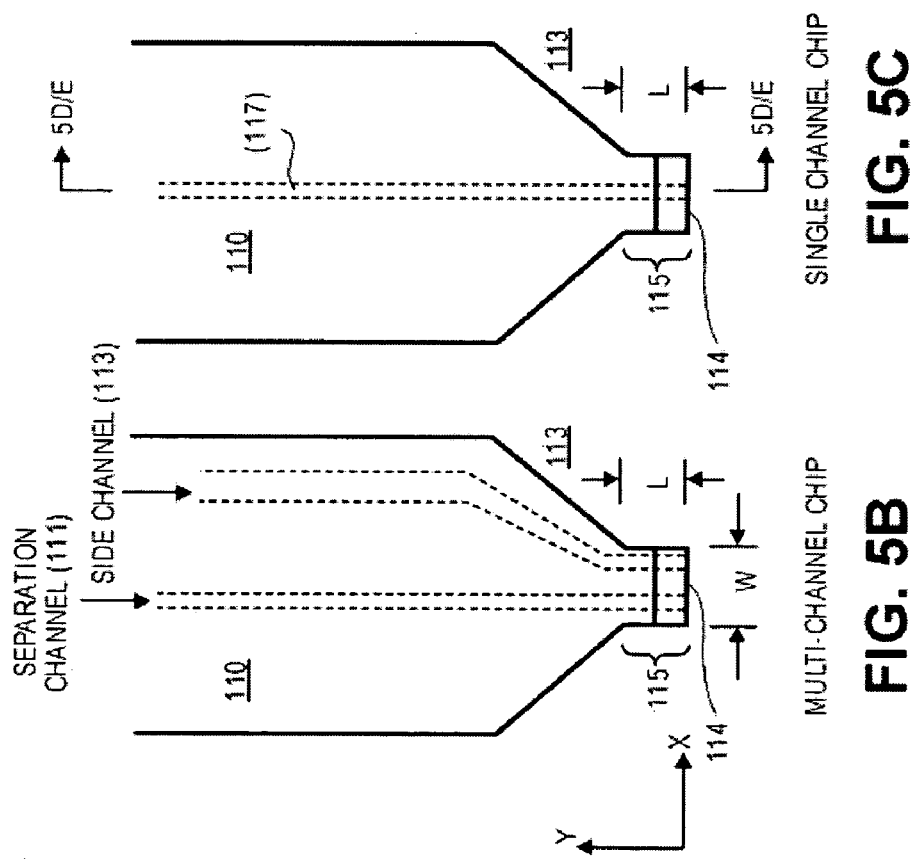

MICROFLUIDIC CHIP WITH ENHANCED TIP FOR STABLE ELECTROSPRAY IONIZATION

CROSS-REFERENCE

This patent application is a continuation-in-part application of U.S. application Ser. No. 10/649,350 filed Aug. 26, 2003, now U.S. Pat. No. 6,803,568, entitled "Multi-Channel Microfluidic Chip for Electrospray Ionization" which is herein incorporated by reference in its entirety.

FIELD OF THE INVENTION

The invention relates to microfluidic chips for electrospray ionization applications. More particularly, the invention relates to improved electrospray ionization tips for mass spectrometric analysis.

BACKGROUND OF THE INVENTION

Electrospray ionization is used to produce ions for mass spectrometry analysis including ions that are derived from relatively large complex molecules such as proteins and nucleic acid molecules. During the electrospray ionization procedure, a sample solution is exposed to an electrical field that charges the surface of the liquid and emerges from an electrospray tip or needle. A spray of finely dispersed charged droplets is thereby generated that is suitable for analysis by a mass spectrometer. The need for conducting high-throughput analysis of relatively small biological samples has led to the development of microfluidic chip devices for electrospray ionization applications.

Microfluidic chips are often constructed using well-known techniques employed in the semiconductor industry such as photolithography, wet chemical etching, and thin film deposition. These devices conveniently support the separation and analysis of sample sizes that are as small as a few nanoliters or less. In general, these chips are formed with a number of microchannels that are connected to a variety of reservoirs containing fluid materials. The fluid materials are driven or displaced within these microchannels throughout the chip using electrokinetic forces, pumps and/or other driving mechanisms. The microfluidic devices available today can conveniently provide mixing, separation, and analysis of fluid samples within an integrated system that is formed on a single chip.

There are numerous design alternatives to choose from when constructing an interface for microfluidic chips and electrospray ionization mass spectrometers. Some electrospray ionization interfaces include microfluidic chips that attempt to spray charged fluid droplets directly from the edge of the chip. But the accompanying solvent is known to wet much of the edge surface of the chip so as not to offer a high-stability spray for many applications. Other attempts to spray ionized particles directly from the edge of a microfluidic chip edge therefore rely on the formation of a hydrophobic surface that can yield improved spray results; however, even that often proves to be insufficiently stable. At the same time, adequate results can be also achieved with other chip devices that incorporate fused silica capillary needles or micro-machined or molded tips. In particular, some recent electrospray ionization designs incorporate small silicon etched emitters positioned on the edge of a microfluidic chip. While it is possible to generate a relatively stable ionization spray for mass spectrometric analysis with some of these microfluidic devices today, they generally require apparatus that is relatively impractical and economically unfeasible for mass production.

A high performance electrospray ionization device is therefore needed for mass spectrometry applications that can be economically produced using large scale manufacturing processes.

SUMMARY OF THE INVENTION

The invention provides methods and apparatus related to microfluidic chips and electrospray ionization applications. Various aspects of the invention can be appreciated individually or collectively to provide an effective interface for microfluidic systems and mass spectrometers or other analytical devices.

A preferable embodiment of the invention provides microfluidic chips that are formed with individual fluid channels. These fluid channels extend through the body of the microfluidic chip and converge at a common distal tip region. The distal tip region includes an open-ended distal tip formed along a defined surface of a microfluidic chip body. The microfluidic chip may be constructed from a pair of polymer plates in which the converging channels run through and lead up to the distal tip region. The microfluidic chip can be also formed with multiple but separate channels that supply fluids such as samples and sheath flow solutions to a single common electrospray tip.

In accordance with another embodiment of the invention, a recessed electrospray ionization tip is provided that is formed along a defined edge of a microfluidic chip. The electrospray device may include a separately formed tip constructed from a shaped thin-film that is bonded to and in between a pair of polymer layers. The separately formed tip may be formed with an exposed distal tip region at which multiple fluid channels converge. The tip may further include fluid channels that are respectively aligned with corresponding fluid channels that are embossed or otherwise formed within the microfluidic chip.

The invention further provides single-use disposable microfluidic chips that are reliable, reproducible and easy-to-use. These microfluidic chips may be selected for sample separation and electrospray ionization processes utilizing electrospray emitters that are formed as an integral part of the chip. These embodiments of the invention reflect a chip design that provides an economical and effective solution that can be reproduced on a large scale production. Many microfluidic chips can be fabricated in batch quantities thus reducing the number of time-consuming steps in forming electrospray emitters and tips.

Another embodiment of the invention provides microfluidic chips that are formed with tapered electrospray ionization (ESI) tips. A series of fluid channels can be formed along a body layer of the microfluidic chip in selected linear or non-linear arrangements terminating at a tapered distal tip region. A separate laminate layer can be selected to substantially enclose the grooves or fluid channels and also extend beyond an end surface of the adjoining body layer of the microfluidic chip. The ESI tips herein may be formed with a laminate layer component and/or a body or channel layer component. These microfluidic chips can be also formed with single or multiple separate channels that supply sample fluids and sheath flow solutions or other fluid materials to single or multiple electrospray tips formed with tapered open-ended distal tip portions.

Another aspect of the invention provides methods of manufacturing microfluidic devices with separately formed ESI emitters. The microfluidic devices may be readily manufacturable following a mass production molding process. Many individual fluid devices may be fabricated at the same time using techniques similar to the manufacture of semiconductor chips for microprocessors. A metal-coated thin film polymer may be separately formed and bonded to polymer plates which are later separated into individual microfluidic devices by cutting apparatus. These and other embodiments of the invention provide convenient fabrication methods for economically manufacturing microfluidic devices for electrospray ionization applications.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

BRIEF DESCRIPTION OF THE FIGURES

The illustrations included within this specification describe many of the advantages and features of the invention. It shall be understood that similar reference numerals and characters noted within the illustrations herein may designate the same or like features of the invention. The illustrations and features depicted herein are not necessarily drawn to scale.

FIGS. 3B and 3C illustrate another embodiment of the invention formed with an extended substrate portion formed with an electrospray tip.

FIGS. 4A–4D are illustrations of a microfluidic chip with tapered channel layers that can be combined with a laminate layer formed with a distal tip groove.

FIGS. 5A–5E are illustrations of microfluidic chips formed with channel layers having an extended platform section.

DETAILED DESCRIPTION OF THE INVENTION

Figure 1:
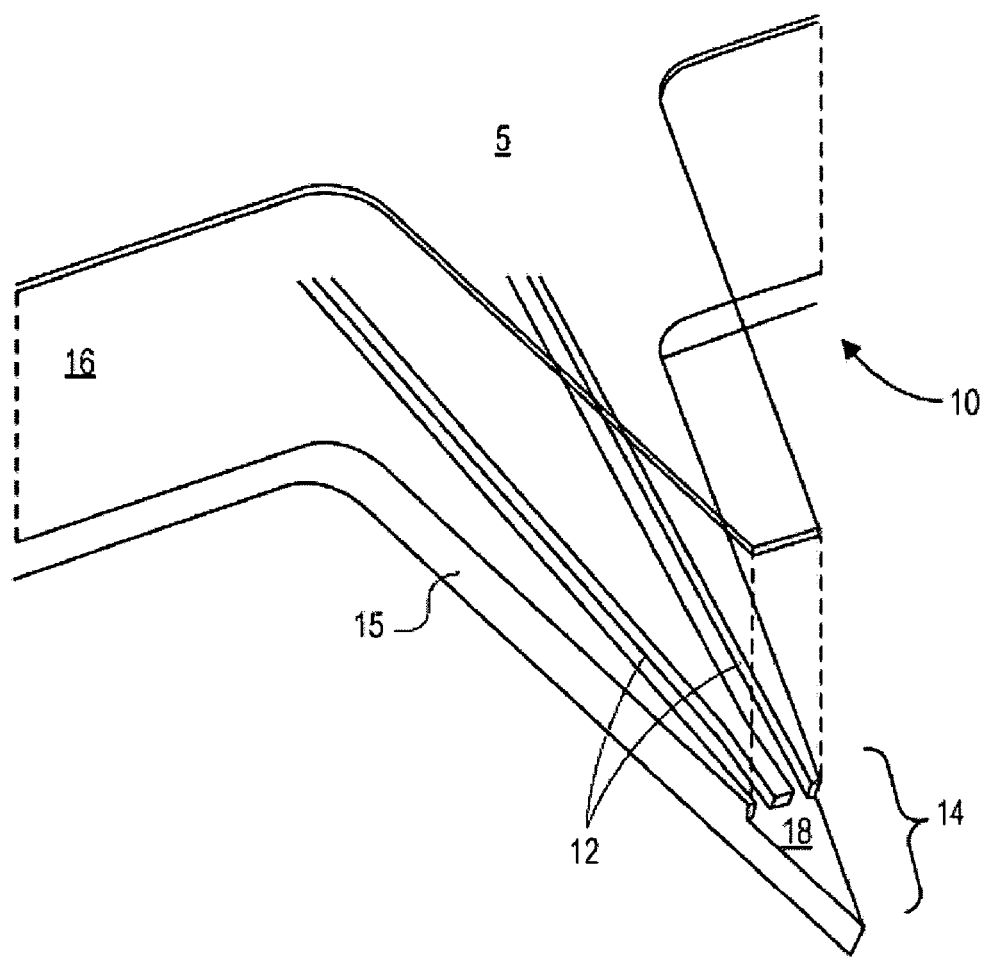
FIG. 1 is an enlarged perspective view of a microfluidic chip that is formed with a tip and a pair of fluid channels converging at a distal tip region in accordance with the invention.

FIG. 1 illustrates a microfluidic chip 10 for electrospray ionization (ESI) applications that is formed with multiple fluid channels 12 converging at a distal tip region 14. The fluid channels 12 may be formed on a substrate layer 16 of the chip 10 that is composed of glass, quartz, ceramic, silicon, silica, silicon dioxide or other suitable material such as a polymer, copolymer, elastomer or a variety of commonly used plastics. The channels 12 can be created using a variety of methods, such as conventional semiconductor processing methods including photolithographically masked wet-etching and photolithographically masked plasma-etching, or other processing techniques including embossing, molding, injection molding, photoablating, micro-machining, laser cutting, milling, and die cutting. A variety of channel patterns and configurations may be also selected for the channels, including channels having a substantially rectangular, trapezoidal, triangular, or D-shaped cross-section. For example, these channels may be produced with an anisotropically etched silicon master having a trapezoidal or triangular cross-section. A channel having a D-shaped cross-section may be formed alternatively following isotropic etching processes. The pair of channels 12 formed on the substrate layer 16 can run relatively non-parallel as shown with respect to each other which substantially converge at the distal tip region 14. A thin film laminate 5 encloses the channels 12 which can be bonded to the substrate layer 16. The thin film 5 is formed so as to terminate at the end of the channels 12 at the distal tip region 14. The distal tip region 14 of the ESI tip 15 may be formed with an open-ended construction where different fluids can emerge or emit therefrom for analysis by a mass spectrometer or other analytical apparatus.

There are numerous advantages in forming multiple channels that meet at a single tip on a microfluidic device. For example, this type of construction may enable analysis of several fluid samples in sequence on the same ESI tip. A calibration solution may be selected among these fluids to adjust the operating conditions of the ESI tip before the sample under test is analyzed. The calibration solution can be used in automating this process of adjusting and optimizing the positioning or conditions of the electrospray, including the physical location of the tip relative to the mass spectrometry instrument and the applied voltage. A calibration solution may also be provided to calibrate the mass spectrometer for mass accuracy, and thereby improve the performance of the instrument. An advantage of carrying out an optimization process on the same tip to be actually used for the samples under test is that the need for and repositioning of another tip may be avoided. Moreover, the ESI tips may each have a slightly different geometry and location relative to the mass spectrometer in some instances that would require additional alignment and repeated optimization. These and other drawbacks are avoided with the microfluidic chips provided in accordance with this aspect of the invention.

The electrospray devices described herein preferably include emitter tips 15 having an open-tip region 18 with converging multiple fluid channels 12. In accordance with this embodiment of the invention, ESI tips 15 do not have an enclosed distal tip region 18 and can thus allow fluids to flow along the external surface thereof. A microfluidic chip 10 formed with an open-tip emitter as described herein possesses another distinctive feature in that the multiple channels 12 leading up to this distal tip area intersect at the tip 15 instead of connecting within the body of the chip. By connecting the converging channels 12 at the open distal end 18 of the spray tip 15, the fluid movement within a single channel will not disturb flow in other channels within the chip body. For instance, the application of pressure to a calibration solution source will induce flow within the respective internal channels, and eventually out of the ESI tip. But this separate calibration solution flow does not interfere with a separate sample channel or other fluid channel formed within the same microfluidic chip. For certain applications where multiple channels leading to a single distal tip are used to supply a series of distinct samples in a sequential manner one after the other, the invention provided herein eliminates or reduces the possibility of cross-contamination between fluid samples. The distinct multiple channels are not in fluid communication with each other within the chip or otherwise connected, but rather they lead to and converge at the common tip structure. In this manner, the samples under test and other solutions are not mixed or become cross-contaminated with each other within in the microfluidic device itself. Accordingly, each fluid can be independently electrosprayed from the same open tip structure outside and beyond the closed channels of the device body into a mass spectrometer for testing and analysis.

The substrate portions 16 for the edge-emitting ESI tips described herein may be integrally formed or separately fabricated and assembled. For example, the tip 15 may be constructed of a thin film polymer or other material that is different from that selected for the substrate portion of a microfluidic chip. The tip may be subsequently assembled with the substrate portion and an adjoining outer layer in accordance with known fabrication methods such as those described in Kameoka et al, An Electrospray Ionization Source for Integration with Microfluidics, Anal. Chem. 2002, vol. 74, pp. 5897–5901, which is incorporated by reference herein in its entirety. The substrate portion may be formed with a relatively rectangular configuration having an end surface on which a separately etched or formed tip may be attached. The fluid channels formed along the substrate portion may be formed with apertures which lead up to the separately formed electrospray tip. The tip component can be formed separate and apart from the channel apertures, and thus, the microfluidic chip body may be formed with more than one channel each having a separate aperture that is coupled with others at a common tip region. For example, a triangular-shaped tip may be separately etched from a thin-film using lithographic techniques and positioned in alignment with the two or more microfluidic channels formed in the chip body. Alternatively, such thin film tips may be cut from polymers that are available in very thin films, such as polyimide (Kapton®) or polyester (Mylar®). These films may be cut using methods such as laser cutting or die cutting. The tip may serve as a fluid wick that protrudes from the edge of the microfluidic chip to provide an edge emitting ESI tip. The ESI tips provided in accordance with the invention assist in the formation of a relatively stable Taylor cone at the apex of the tip which provides an improved electrospray ionization source for analytical apparatus such as mass spectrometers. Alternatively, a substrate layer can be formed with a pointed distal tip portion with a relatively planar top surface on which a separate channel layer can be added to define the fluid channels. The channel layer may be etched by known techniques to form the plurality of fluid channels leading to the distal tip region. When it is preferable however to manufacture a single piece substrate, the ESI tip may be formed with a monolithic construction as a pointed extension protruding from the edge of the chip. Regardless of which manufacturing process is selected for forming the substrate portions of the ESI tips herein, a laminate or top layer may be bonded or otherwise attached to the substrate portion in order to enclose the fluid channels leading up to but excluding the converging distal tip region which should remain open-ended and exposed.

Figure 2:
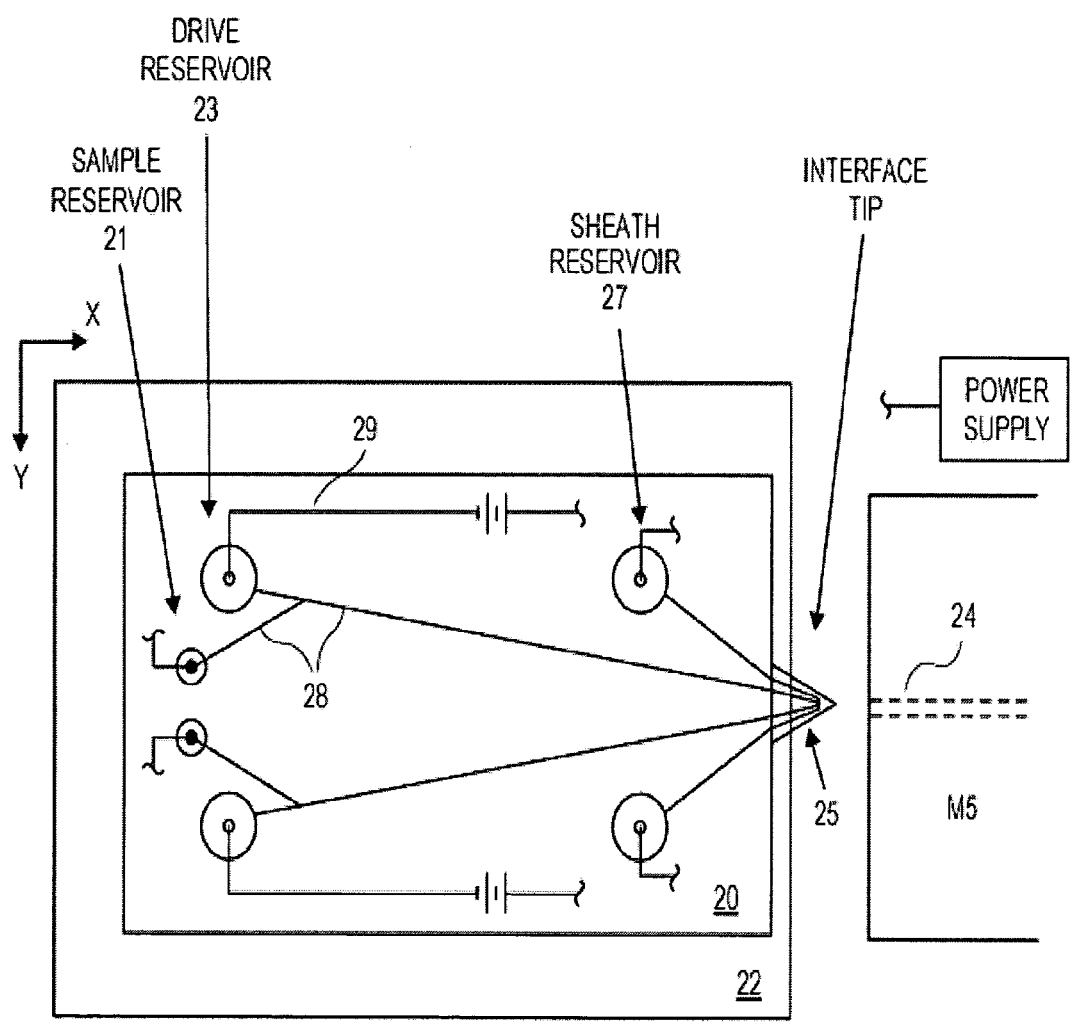
FIG. 2 is a simplified top view of a table mounted microfluidic chip that is formed with a tip for directing ionized spray into a neighboring mass spectrometer.

As shown in FIG. 2, the microfluidic devices provided in accordance with the invention can be incorporated into an ESI system for mass spectrometry analysis. A microfluidic chip 20 can be mounted as illustrated on a XY table or other adjustable platform 22 that is adjacent to a mass spectrometer (MS) such as an ABI Mariner time-of-flight (TOF) instrument. The table mounted microfluidic chip 20 can be formed with a tip 25 for directing ionized spray into the MS. The table 22 may be positioned and adjusted as needed to direct the device tip 25 and electrospray emissions into the capillary portion or receiving orifice 24 of the MS. In addition, the microfluidic chip 20 may be formed with one or more reservoirs that hold various fluids to be analyzed or run through the MS. The chip 20 may include a plurality of sample reservoirs 21, drive reservoirs 23 and sheath reservoirs 27. Each of the reservoirs may be fluidly and separately connected to a fluid channel or microchannel 28 formed within the chip body. An electrode 29 connected to a power source may be inserted into a reservoir so that a voltage is applied between the chip reservoir and MS. Electrodes may also be deposited and patterned on one of the polymer surfaces, preferably to contact the solution at the tip. A fluid pump may also be selected to impart the flow of fluids within the network of individual channels within the chip body. Each of the channels 28 within the body converge and lead to a common emitter tip 25 that also includes an enclosed portion that prevents cross-contamination of fluids. The emitter tip 25 however is also formed with a relatively open-distal tip portion that permits fluids originating from different reservoirs from within the chip body to emanate from a common ESI tip into a nearby MS for analysis. An improved ESI interface is thus provided in accordance with the invention that is different from previous arrangements including those with mass spectrometers directly connected to a microfluidic microchip.

An electrospray interface generally allows liquid substance specimens to be ionized before they are presented for mass spectrometry detection. Electrospray ionization generates ions for mass-spectroscopic analysis of various materials including chemical or biological specimens. The ESI process typically involves the emission of a liquid into a capillary at the input of a mass spectrometer from the spray tip that is subjected to an electrical potential having a range of values ranging from approximately 1–7 kV (kiloVolt). This potential can be controllably varied as part of a feedback loop to provide an electrospray with improved stability. The high electrical field generated thus induces charges on the surface of the liquid in the area of the spray tip. When this field is high enough, the liquid at the tip takes on the shape of a cone often referred to as a Taylor cone. The spraying of the fluid substance in the vicinity or area of the spray tip generally occurs when the Coulombic forces are great enough to overcome the surface tension forces present in the liquid. This spray occurs in the form of a thin jet of liquid at the tip of the Taylor cone. It has been observed that ionization by means of ESI for flow rates such as typically arise in microfluidic structures (10–1000 nl/min) do however require relatively high electrical field strengths. Accordingly, relatively fine spray tips with a diameter of about 10–100 μm are often required to cause ionization.

To carry out electrospray ionization mass spectrometry, the microfluidic chip 20 is positioned so that the distal end of an interface tip 25 is often placed a few millimeters (e.g., 1–4 mm) from the mass spectrometer (MS). The microfluidic chip 20 formed with an interface tip 25 in accordance with the invention as shown in FIG. 2 is positioned such that the interface tip is aligned with the MS. A sample is introduced into a sample introduction reservoir 21 using a suitable sampling device such as a micropipet or syringe. Furthermore, in order to carry out electrospray ionization process, a relatively high voltage and low current power supply can be selected to apply a voltage, e.g., 3–5 kV, with a driving reservoir electrode that can be inserted in the driving reservoir 21. Meanwhile, the sample introduction reservoir 21 is held at a lower voltage than driving reservoir 23 via a sample introduction reservoir electrode inserted in the sample introduction reservoir 21. For example, when a driving reservoir is held at 5 kV in one embodiment of the invention, a sample introduction reservoir is typically held at 6–7 kV. This drives the sample solution from a sample introduction reservoir through a distinct channel pathway towards a driving reservoir. Next, the power to the sample introduction reservoir may be turned off while the driving reservoir 23 is held a 5 kV, and in turn, a lower voltage than the driving reservoir is applied to a sheath liquid via an electrode inserted in the sheath liquid reservoir 27. The current path is from the driving reservoir 23 to the sheath liquid reservoir 27 via the interface tip 25. The sheath liquid reservoir 27 is held at 1–2 kV or ground. This drives the sample through its respective channel towards an outlet through the interface tip 25 and will eventually exit from an ESI tip opening formed with an open-end construction in accordance with an aspect of the invention. As the sample exits the tip opening, it is sprayed into the entrance capillary portion 24 of a mass spectrometer (MS) thus permitting its analysis. The voltage applied to the sheath liquid causes a Taylor cone to form at the interface tip 25 from which ions are generated by electrospray. The sheath liquid flow may be produced by applied pressure, electrokinetic flow or capillary action.

Figure 3A:
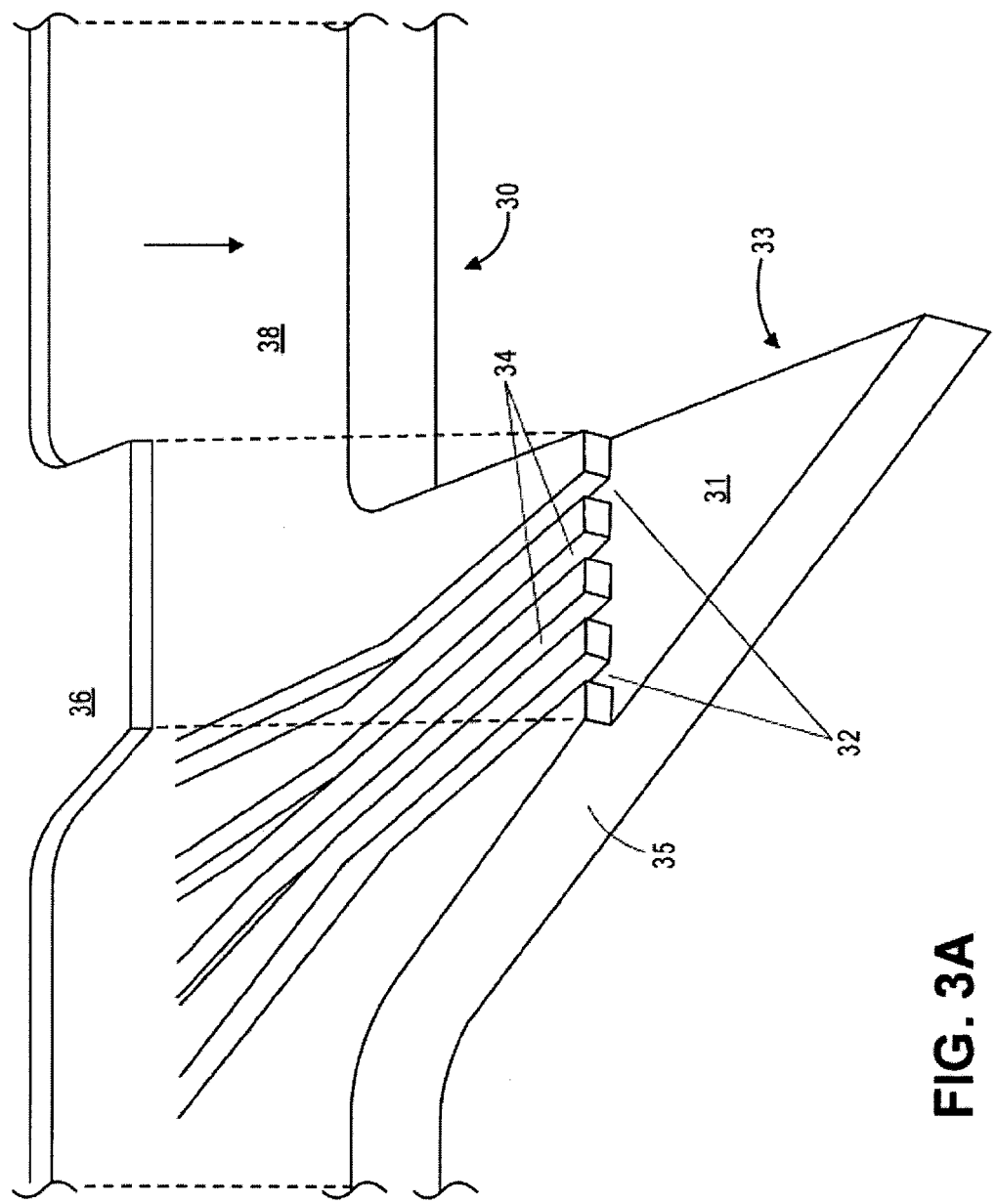
FIG. 3A is a perspective illustration of a microfluidic chip formed with a tip region and multiple fluid channels converging thereon.

As shown in FIG. 3A, another embodiment of the invention provides a partially-exposed ESI tip 35 formed on a microfluidic chip 30 with multiple channels. The ESI tip channels may be formed by embossing techniques or other known processes to provide four or more separate converging channels. A pair of relatively outer channels 32 may be selected for a sheath flow to assist in the electrospray process, and a pair of relatively inner channels 34 may be used for a sample solution and a calibration solution. The plurality of channels can be formed along the microfluidic chip body in even-numbered pairs (2×) to provide 2, 4 or more fluid channels. The channels may converge at an embossed recessed tip 33 as shown to carry out microfluidic chip based ESI. It shall be understood however that the invention herein is not limited only to those embodiments illustrated and shall include electrospray devices formed with any even or odd-number of fluid microchannels leading to and converging at a open-ended distal tip.

Furthermore, the microfluidic chips provided herein may be formed by various embossing, molding, injection molding, or casting processes in accordance with the invention. These processes typically begin by etching a master in a material chosen to allow convenient and accurate microfabrication, such as glass or silicon. The etching is photolithographically patterned, and can use wet chemical etching, vapor phase etching methods, or plasma etching. One example of a method which yields good channel profiles is the deep reactive ion etching (DRIE) of silicon substrates. The master etched in this way can then either be directly replicated by the methods listed above, or a replica of the master may be made using an electroforming process, typically using nickel or a nickel alloy. One advantage of using an electroform is that it is more robust and less breakable than a glass or silicon wafer. It also inverts the surface profile. The electroform can then be used to make the final patterned device in the material of choice, typically a polymeric material that can be embossed, molded, or cast. There are also other materials, such as certain glasses that can be patterned by embossing or casting. The microchannels and the open-ended portion of the ESI tip shown in FIG. 3A may be formed with a two-depth etching process of a silicon master. This method may consist of at least two deep reactive ion etcher (DRIE) etching steps on a silicon master, each with its own lithographically defined masking pattern. The ESI tip may be formed by initially selecting a relatively thick polymeric layer ranging from approximately 0.5 to 2 mm in which the microchannels can be defined. A first etch step may be performed to create a multiple microfluidic channels that are etched to selected depths that can generally range from approximately 20 to 30 µm. A second etch step may be then completed to form open-end distal tip area that is etched to a selected depth that can range from approximately 100 to 300 µm. This second etch may extend to the edge of the microfluidic chip to define a sharp distal tip region where the microfluidic channels converge to provide a single multi-channel ESI tip. The three-dimensional patterning that is created by these multiple etches on a silicon master is then replicated into a polymeric substrate, through the intermediate of an electroform, as described above.

The microfluidic channels described herein may be further designed and fabricated by various known techniques and apparatus such as silicon master systems. A series of one or more channels may be formed with a predetermined depth following a methodology that can include the following steps: (1) defining a fluid channel design with a computer aided design (CAD) program, and constructing a photomask that is patterned after the selected design; (2) performing the photolithographic patterning of a photoresist layer on a silicon wafer or substrate using the constructed photomask; (3) etching the silicon in a deep reactive ion etcher (DRIE) to a selected depth such as 30 µm or greater to form channel structures with substantially straight sidewalls; (4) creating a negative version or electroform of this channel structure with nickel using techniques such as electroplating; (5) embossing the channel electroform into a sheet of polymer such as Zeonor at a relatively high temperature and selected pressure (Zeonor and other similar polymers may preferably have good solvent resistance and low water adsorption which are desired for mass spectroscopy applications); (6) forming or drilling well holes and fluid reservoirs into the polymer sheet as needed in relation to respective embossed channels; and (7) bonding a second, unpatterned, polymer sheet to the first sheet in order to enclose the channels. It shall be understood that other methods and variations of the preceding steps may be modified in accordance with the concepts of the invention. For example, it may be preferable to further treat the fluid channels with materials to improve observed performance characteristics. The channels may be modified in some instances to provide a more hydrophilic surface than can improve the electrospray performance of microfluidic devices. During the manufacturing process, a series of one or more open channels may be coated by slowly introducing a coating solution flowing from within the chip outward. An example of a suitable coating such as polyvinyl alcohol can be applied to the channel surfaces and thermally immobilized to remain in place for a sufficient period of time. By treating the channel surfaces in this manner, it may be possible to minimize or reduce protein adsorption and to prevent the emitted solutions from spreading to undesired portions of the microfluidic chip. A more stable and controlled electrospray may be thus provided as intended by the defined dimensions and configuration of a selected fluid channel.

The microfluidic chips provided in accordance with the invention herein may include an outer layer 36 formed of a relatively thin laminating film for enclosing the plurality of microchannels 32 and 34 as shown in FIG. 3A. This thin film layer 36 may be bonded or otherwise attached to a substrate layer 38 embossed with the convergent fluid microchannels. The converging microchannels may generally lead up to an open-tip region 31. The open-tip region 31 may be defined by a generally flat external surface formed on the substrate layer of the microfluidic chip. This region 31 can be formed by laminating the substrate layer 38 with a film 36 that is shaped and formed with dimensions so as to end just short of or at the base of the tip 33 as shown. A variety of preferably pointed configurations may be selected for the open-tip region 31, including a substantially triangular shape as illustrated. The outer layer 36 may be generally formed with a similar pattern as the substrate layer 38 but may extend only up to the base of the tip 33 thus forming an exposed area or open-tip region 31. The laminating cover layer 36 may thus cover over an underlying substrate polymer 38 to create a series of closed channels. For example, a top layer may consist of a thin sheet of Zeonor that may be bonded to the underlying substrate at lower values of temperature and pressure than when it is used as a selected material for embossing processes. The microfluidic chips herein may be laminated using a thin Zeonor film to seal the fluid channels that terminates near the base of the tip region. These tips provide open structures having a plurality converging channels that terminate with fluid openings intersecting at a common distal tip region. Various fluid materials may be thus directed through respectively defined fluid microchannels within the chip that lead up to and exit from a common distal tip.

With respect to another embodiment of the invention that is also shown in FIG. 3A, some of the multiple converging fluid channels leading to the distal tip region of the microfluidic chip may be selected to introduce a sheath flow solution. A pair of outer microchannels 32 may be selected to introduce a sheath flow of organic solvent to optimize the electrospray process. In general, sheath flows are designed to assist during the electrospray process and are commonly used to couple conventional capillary electrophoresis (CE) instruments to mass spectrometry (MS). A sheath flow provides numerous advantages including an ability to lessen the strict requirements on salt concentration, and fraction of organic solvent in CE separation. Since the electrospray process typically requires a constant flow of solution to achieve a suitable spray, a sheath flow may be provided to make up the difference when the CE separation is purely electrophoretic with no bulk flow of solution. In general, sheath flows typically use a mixture of aqueous buffers and non-aqueous solvents such as methanol, isopropanol, or acetonitrile. The advantages provided sheath flows can be similarly recognized when applied to microfluidic chips provided in accordance with the invention. Moreover, a sheath flow may be effective at relatively lower flow rates with some of the two-dimensional tip geometries described herein in comparison to those commonly used in conventional sheath flow interfaces. A 1:1 ratio of flow rates could be quite effective with the tip designs described herein, for example, as opposed to conventional sheath flow devices which often operate at 10:1 to 100:1 dilution ratios. The dilution of analyte with sheath flow designs provided in accordance with this aspect of the invention may be relatively minimal when compared to currently available sheath flow devices. Accordingly, the resulting loss of sensitivity can be greatly reduced with the low flow rates that can be achieved for the sheath flows generated by the microfluidic chips herein.

Another embodiment of the invention is shown in FIGS. 3B–C that provides an electrospray tip 37 formed with an extended substrate portion 39. As illustrated in FIG. 3B, a microfluidic chip 40 may include a plurality of channels 42 formed in a relatively thicker body layer 44 in accordance with fabrication methods described herein. A series of four channels with a substantially square shaped cross-section may be formed to direct various solutions to the ESI tip including samples and sheath fluids. FIGS. 3B–C further show that the ESI tip 37 may be formed with channels 42 running along a relatively bottom surface of the body layer 44 and terminating at a substantially flat end surface 47. In addition, a relatively thinner substrate layer 46 having a thickness of less than 1.0 mm can be bonded or laminated to the body layer 44 to enclose the channels 42. The substrate layer 46 includes an extended substrate portion 39 formed with a point 48 thus providing an exposed open-area region 41 for the ESI tip.

Figure 3D:
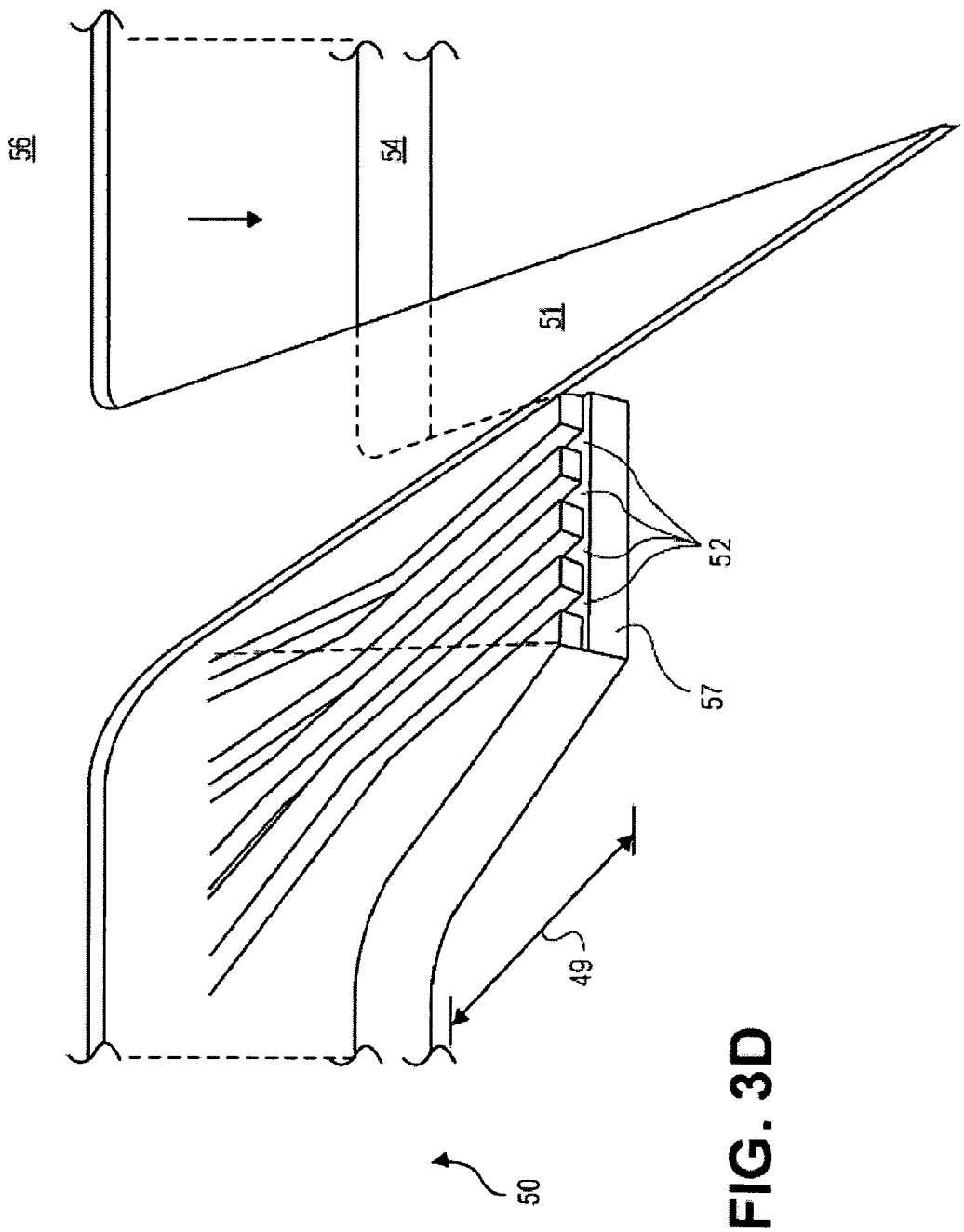
FIG. 3D is a perspective illustration of a microfluidic chip having an extended thin top layer forming an electrospray tip and a bottom layer terminating at a flat edge where multiple fluid channels end.

In accordance with yet another embodiment of the invention, a microfluidic chip 50 may be formed with an ESI tip having an extended top laminate layer 56 as shown in FIG. 3D. As with other variations of the invention provided herein, a substrate layer 54 may include a plurality of microchannels 52 which terminate at the substantially flat end surface 57 of a short substrate extension 49. The microchannels 52 can be formed along a relatively top surface of the substrate layer 54 and enclosed by the thin top laminate layer 56. The ESI tip may include a relatively thin lamination film having a thickness of less than 1.0 mm. The top layer 56 further includes a pointed tip portion 51 which extends beyond the edge of the relatively 54 thicker substrate layer in which channels 52 are embossed or otherwise formed. This embodiment of the invention may be formed as described above with respect to FIG. 3A except that the top layer 56 is not truncated but is rather formed with the pointed tip portion 51 extending past the flat end surface 57 of the substrate extension 49 at which the multiple fluid channels 52 terminate.

It shall be understood that various concepts of the invention can be incorporated with known microfluidic devices or microchips selected for applications such as capillary electrophoresis (CE)/mass spectrometry MS via electrospray ionization (ESI). Many devices offered today adhere to a "thick-to-thick" approach, either using glass or plastic materials. Such an approach traditionally involves combining multiple device layers each having relatively thicker dimensions ranging from approximately 600–2000 μm. Electrospray tips provided herein can be selected in place of or combined with what is available today such as microfluidic devices formed with a capillary tube attached to the end of a fluid channel, a separate thin film formed or machined with a tip sandwiched between relatively thicker plates, or machining the tip itself from a thick plate. Depending on the varying thickness of the formed electrospray tips today, some relatively thinner formed tips may be characterized as 2D tips (two dimension) while other relatively thicker tips can be referred to as 3D tips (three dimension). Another aspect of the invention provided herein includes microfluidic devices formed with monolithic tips for electrospray which may be characterized as 2.5D tips formed with an intermediary thickness and a multi-layer tip geometry. These electrospray tips may include a selected tapered geometry with tip features that achieve an improved and more stable electrospray. Such geometries can help minimize the dead volume observed at the tip end and reduce the on-set voltage for an electrospray. The microfluidic chip tip designs herein also lend themselves to reliable mass production techniques, and may thus significantly increase the chip-to-chip reproducibility of such designs. It shall be understood that tip designs provided herein can be applied both to single channel and multi-channel microchips, including those providing for sheath flow.

As shown in FIG. 4A, a microfluidic chip 80 composed of two basic layers is provided in accordance with this aspect of the invention. The microfluidic chip can be formed with a channel layer 82 having various channels 85 and reservoirs as described elsewhere herein. In addition, a separate sealing film layer 84 can be provided to seal the respective bottom portions of channels 85 and reservoirs to form an enclosed microfluidic network within the device. The channel layer 82 can further include a plurality of reservoirs for containing various fluid media that can be also formed within the body layer so that each channel is in fluid communication with one or more reservoirs but not necessarily in fluid communication with each other within the boundaries of the channel or body layer. Moreover, the sealing film or enclosure layer 84 may be provided to enclose at least a portion of the separated channels 85 formed within this body layer 82. The enclosure layer 84 can further include an exposed open-tip extension 88 extending beyond a tapered end portion of the body layer. The open-tip extension 88 can be also formed with a tip groove or notch 81 thereon as part of an electrospray ionization tip at which the plurality of separated channels also terminate to direct an ionization spray from the microfluidic chip. During manufacturing and formation of this tip extension 88, it can be machined, milled, cut or otherwise formed as part of the enclosure layer 84 to provide a single-piece monolithic electrospray tip. Alternatively, the exposed tip extension 88 and the enclosure layer 84 can be separate pieces of material that are bonded or otherwise joined together.

The electrospray tip portion provided with this aspect of the invention can be described as being formed with a single or two-part construction: a covering or laminate layer component; and/or a body or channel layer component. The geometry of each component may provide a more stable electrospray when used separately or in combination with each other. The laminate layer component of the tip can further include a tip groove or nub formed on an open-tip extension thereto which can be micro-machined or otherwise formed to also provide a reliable electrospray tip. Furthermore, the channel layer component includes a single or dual tapered end portion where one or more channels formed therein terminate. This channel layer tip feature can provide resulting benefits such as confinement of solution coming out from a separation channel and/or a sheath flow channel at the electrospray tip, greater assurances of a more stable spray at the selected sheath flow rate (nl/min) or electrosomotic driven flow (EOF), reduction of dead volume at the electrospray tip, and reduction of the on-set voltage for the electrospray. This aspect of the invention provides electrospray tips that eliminate or substantially reduce sprayed solution from spreading at the tip region and has been observed to produce more stable Taylor cone formation.

Figures 4B, 4C, 4D:
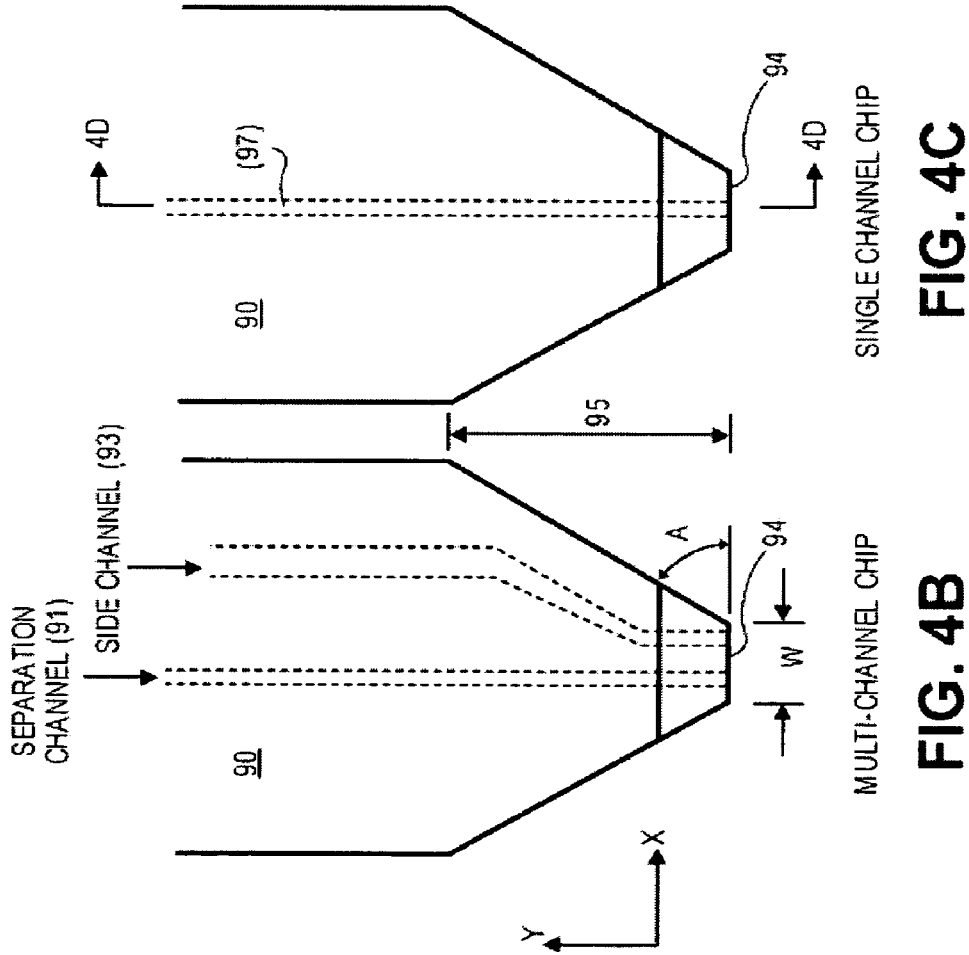

FIGS. 4B–D provides planar views of a microfluidic device channel layer 90. The distal tip portion of the channel layer 90 can be machined or otherwise formed at a selected acute angle (A) ranging between 0–90 degrees, and preferably at an angle approximately 30–70 degrees relative to the flat end surface 94 of the layer as shown in FIGS. 4B–C. The channel or microfluidic body layer 90 may thus be formed with a tapered end portion 95 formed along an X-Y axis as shown that includes a flat truncated portion having a selected width (W). Moreover, a series of one or more microchannels can be formed on the channel layer, which may vary in thickness of up to 1 mm or greater. As depicted in FIG. 4B, a separation channel 91 can be formed in addition to a separate side channel 93. For certain applications, the channel layer 90 may be defined as having two opposite sides separated along a longitudinal or Y-axis as viewed from FIG. 4B such that one or more channels can be formed on one side of the channel layer, e.g., relatively left side of the device, while one ore more channels can be also formed on the other side of the channel layer, e.g., relatively right side of the device. The separation and side channels as shown may terminate at channel openings evenly spaced apart on the end surface of the channel layer, or more particularly, the channels can be spaced from the edge of the end surface 94 or tip portion at the same distance ranging from approximately 10–100 μm. A series of microchannels can be thus formed along a body layer that are enclosed by a covering layer to provide an electrospray ionization tip at which each microchannel terminates to direct an ionization spray from the microfluidic chip. Alternatively, a single channel or separation channel 97 can be formed running along the middle or longitudinal axis of the tip microfluidic device as shown in FIG. 4C. The flat end surface 94 in either embodiment of the chip can be formed with various widths (W), preferably between about 30–500 μm, and more preferably between about 100–300 μm wide. As shown in FIG. 4D, the tip portion 95 of the channel layer can be formed with an initial height (h) or thickness measured along a Z-axis and tapered to a selected tapered height. For example, the tip portion 95 can be milled or formed at an angle (B) of about 30 to 45 degrees along a Y-Z axis relative to the layer surface to form a flat end surface having a height (h1) ranging from approximately 30–500 μm, and more preferably between approximately 50–300 μm. The channels and other structures in these channel layers can be enclosed with a covering or laminate layer described elsewhere herein. These laminate layers can extend beyond the illustrated single or multiple tapered end portions of the microfluidic channel layer to provide an open-ended distal tip portion at which the defined microchannel terminates to provide an electrospray ionization tip that directs an ionization spray from the microfluidic chip.

Another embodiment of the invention is illustrated in FIG. 5A. This microfluidic chip 100 for electrospray ionization may include a channel plate 102 formed with two or more non-intersecting fluid channels 105 that are each in fluid communication with at least one fluid reservoir located within the plate. Additionally, a covering plate can be selected for enclosing the non-intersecting fluid channels 105 formed on the channel plate 102. The covering plate 104 can include an overhang 106 formed with an optional tip groove that extends beyond a tapered end portion 103 of the channel plate 102 to provide a single or dual-tapered tip 107 that includes an open-tip region 108 at which each of the non-intersecting fluid channels terminate. It shall be understood that the overhang 106 can be otherwise characterized as an underhang or underlip depending on the orientation of the microfluidic chip and which plate is facing relatively up or down. The covering plate 104 with the overhang 106 can be positioned and functional either as a relatively top layer or bottom layer of microfluidic devices having two or more layers as provided herein. Furthermore, the channel plates and covering plates herein may be formed of varying thickness and one need not be formed with a relatively greater or lesser thickness than the other. Alternative embodiments of the invention includes devices constructed from either a thin-to-thin or also a thick-to-thin approach. For example, a relatively thicker channel plate formed with a thickness of up to approximately 600–2000 μm or greater can be combined with a covering plate formed with a thickness of up to approximately 10–100 μm or greater. Both the channel and covering plates could also be formed with what may be characterized as relatively thin film layers that can have a thickness of up to approximately 10–100 μm or greater. Furthermore, the channel plate and covering plate components of this embodiment of the invention can be molded, milled or otherwise formed of various a materials including polymers, copolymers, elastomers, ceramics, quartz, silicon, silicon dioxide, silica, and glass. For certain applications, this embodiment of the invention may be also combined with other aspects of the invention including the positioning of the pointed electrospray tips within a recessed portion of the microfluidic chip illustrated in greater detail elsewhere herein.

FIG. 5B illustrates another tip feature provided in accordance with the invention. As with other devices described herein, this device layer 110 can include one or more microchannels to provide at least a separation channel 111 and a side channel 113 to deliver materials to the electrospray ionization tip. The side channel shown can be used alone or with another channel for providing sheath flow solution to the electrospray. In this embodiment the channels can be relatively centered at about 10–100 μm from the edge of an extended platform section 115. Meanwhile, FIG. 5C illustrates a channel 117 formed in the middle of the electrospray tip for single channel chip applications. A monolithic ESI tip portion can be constructed essentially the same way for a multi-channel chip shown in FIG. 5B as the single channel chip shown in FIG. 5C where the separation channel is positioned in the middle of the tip. In either illustrated embodiment, an extended platform section 115 can be formed with a predetermined length (L) and width (W). These dimensions may vary depending up on certain applications, but preferably the length (L) may range from approximately 100 μm–5 mm, and the width (W) may range from approximately 30–500 μm. An end surface 114 may be formed along the extended platform section 115 at which one or more microchannels can terminate as shown. The tip portion 113 as shown leading up to the extended platform section 115 can be formed at selected angles along a defined X-Y axis as with other embodiments of the invention described herein.

As shown in FIGS. 5D and 5E, other electrospray tips provided in accordance with this aspect of the invention can be formed with either single or multiple tapered edges. In addition to or instead of having a tapered width (W) leading up to the electrospray tip portion of the illustrated channel layer shown in FIGS. 5B and 5C, the tip may be formed with a tapered height as illustrated in FIGS. 5D and 5E. The channel layer 110 may be formed with an overall body thickness or height (h) leading up to a narrowed or tapered distal tip portion to the extended platform section. The extended platform section 115 may terminate with an end surface 114 having a relatively reduced height (h1) that may range from approximately 30–500 μm. As depicted in FIG. 5D, the tapered edge of the distal tip portion may be formed at an angle (C) thus providing a single chamfered edge. Angle (C) may be an acute angle ranging from 0–90 degrees, and preferably selected to be 30 to 45 degrees. Alternatively, as shown in FIG. 5E, the distal tip portion of the extended platform section 115 may include a step or ledge 118 when the tapered tip portion is formed at an acute angle (D) which may be an acute angle that is relatively greater than angle (C) or 30 degrees. The step or ledge 118 having a thickness (h1) may be also formed at an angle or with a curvature (E) and lead up to the end surface 114 of the extended platform section 115 as shown in FIG. 5E. The angle or curvature (E) formed on this step or ledge 118 can be milled or otherwise formed with an appropriate tool set to a desired angle or radius (r) which corresponds to the selected curvature or rounded taper at this portion of the extended platform section 115.

Figure 6A:
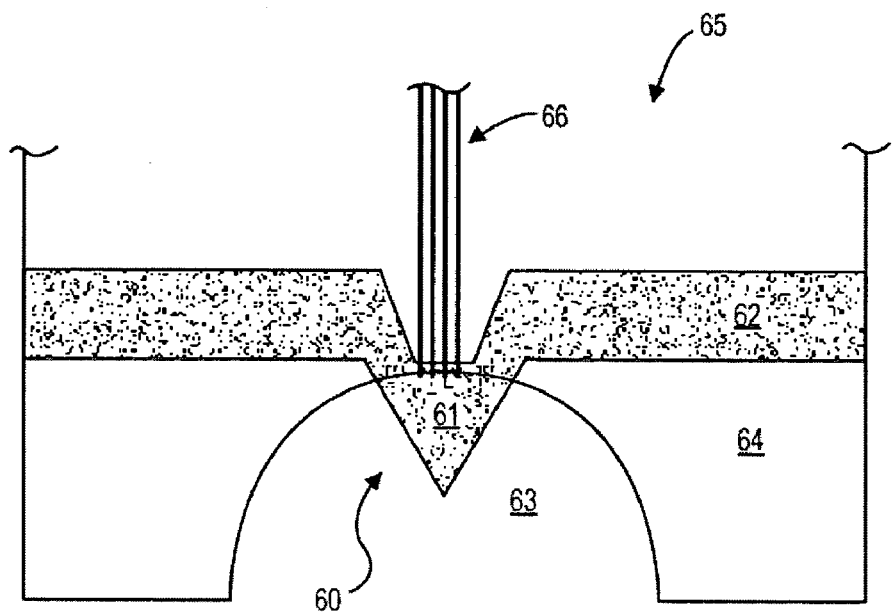
FIGS. 6A and 6B show another embodiment of the invention that provides a microfluidic chip formed with a recessed tip region.
Figure 6B:
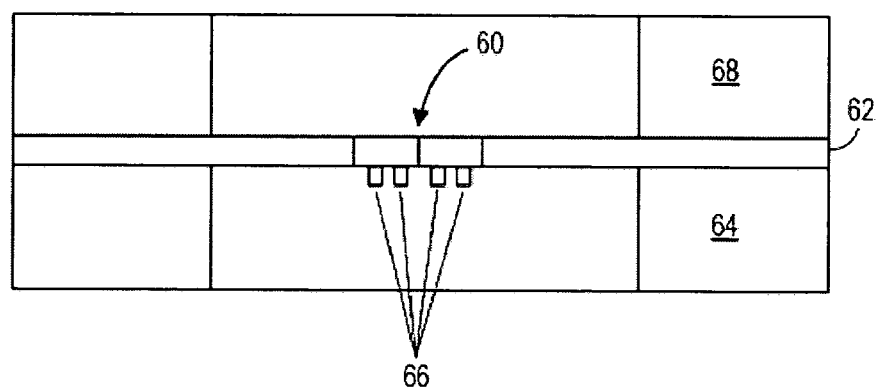

FIGS. 6A and 6B provide close-up views of another embodiment of the invention. FIG. 6A is the top view of an exposed edge-recessed ESI tip 60 that is fabricated from a thin metal-coated polymer film 62. The polymer film 62 is shown with a bottom polymer plate 64 in this illustration without a top laminate layer 68 so as to expose the interior region of the microfluidic device. In this embodiment of the invention, the microfluidic chip 65 includes a thin polymer film 62 that is placed along the edge of the chip body in a recessed area 63. A relatively open distal tip region 61 may protrude from the edge of the device 65 within the protected recessed area 63. A plurality of fluid channels 66 can be formed on a substrate layer 64 or polymer chip which run up to the edge of an opening at the edge of the chip 65. The recessed opening 63 along the edge of the chip may be drilled or otherwise formed with a desired geometric configuration such as a semi-circular pattern. The fluid channels 66 may be formed relatively close together with vertical sidewalls formed by an embossing process that starts with a DRIE etched silicon wafer, as discussed above. For example, a channel design may be selected with four channels each formed 20 μm wide and separated by 40 μm spaces in between. This configuration would only occupy a total width of 200 μm for all of the channels and wall spaces therebetween. Another embodiment of the invention may include the formation of 30 m wide channels that are separated by 100 μm spaces. In this configuration, the total channel and wall width would be 420 μm wide. As observed in the semiconductor chip manufacturing industry, smaller lines widths generally require more demanding and exacting fabrication techniques. It shall be understood however that the relative spacing, width dimensions and the number of channels may be modified in accordance with the invention.

Another aspect of the invention provides a solution to the problem of creating ESI-emitting structures at the edge of a chip that are vulnerable to breakage. As shown in FIG. 6A, the tip structures 60 provided herein may be positioned within a recessed area 63 away from the edge in order to protect it. A recessed ESI tip has both practical and fabrication advantages. For example, the protected tip is often much less susceptible to breakage or contamination than one that protrudes from the chip. The end portion of a recessed channel that is fabricated by molding techniques achieves a generally more reliable edge rather than that formed by a cutting process, which potentially results in the formation of burrs or small fragments of plastic. Based on the fabrication processes selected for prior designs, the recessed tips designs provided herein can be either injection molded or readily formed from a laser-cut polymeric platform. While both recessed and non-recessed ESI tips can be both formed with multiple convergent fluid channels leading to an open-ended distal tip described herein, either may be fabricated and comparatively tested to determine which configuration may provide a relatively more stable spray for certain applications. It shall be further understood that voltages may be similarly applied to drive fluid flow within microfluidic chips having recessed ESI tips as with other embodiments of the invention herein.

FIG. 6B illustrates the side view of the ESI tip 60 that is constructed from a thin polymer film 62 sandwiched and bonded in between two polymer plates 64 and 68. The thin polymer film 62 may be preferably formed of a very thin polymer having a thickness of approximately 10 microns that is sealed between the two relatively thicker polymeric layers 64 and 68. The thin metal-coated polymer film 62 may be selected and bonded to a substrate layer 64 as shown that includes four separate channels 66 leading up to and connected to the tip 60. A pair of relatively outer channels may be selected to provide a sheath flow to assist the electrospray process, and two relatively inner channels may be designated for spraying a sample fluid and a calibration solution, respectively. The sheath flow may be implemented as described elsewhere in this specification in accordance with the invention. It should be noted that the advantages of forming multiple channels leading to a single ESI tip are independent of whether the tip is recessed or not.

Figure 7A:
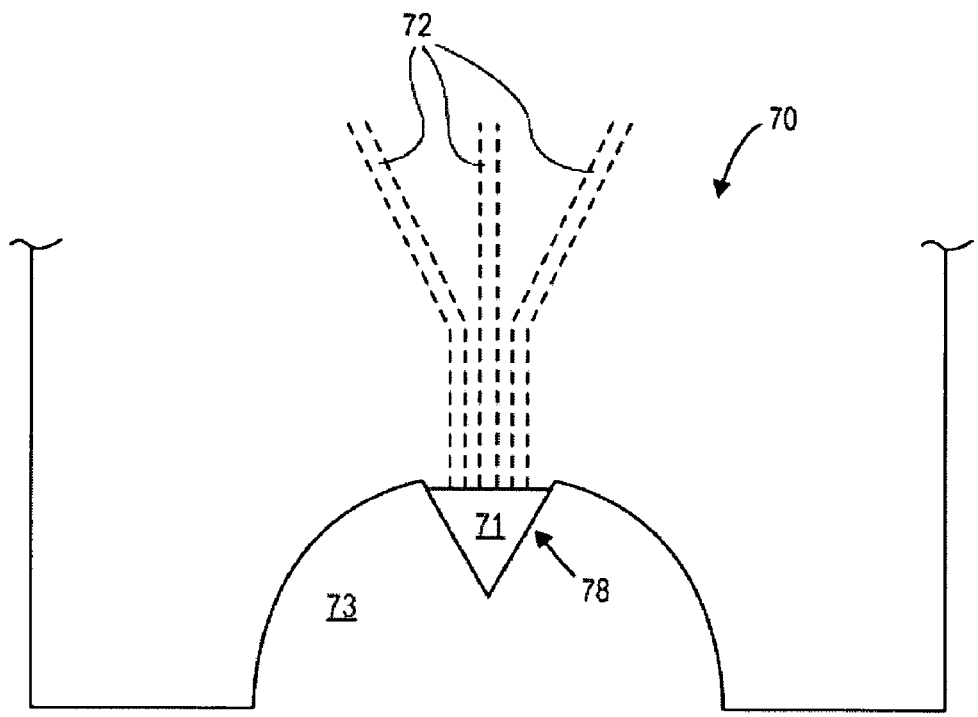
FIGS. 7A and 7B illustrate a microfluidic chip formed with a recessed tip integrally formed with a bottom polymer plate.
Figure 7B:
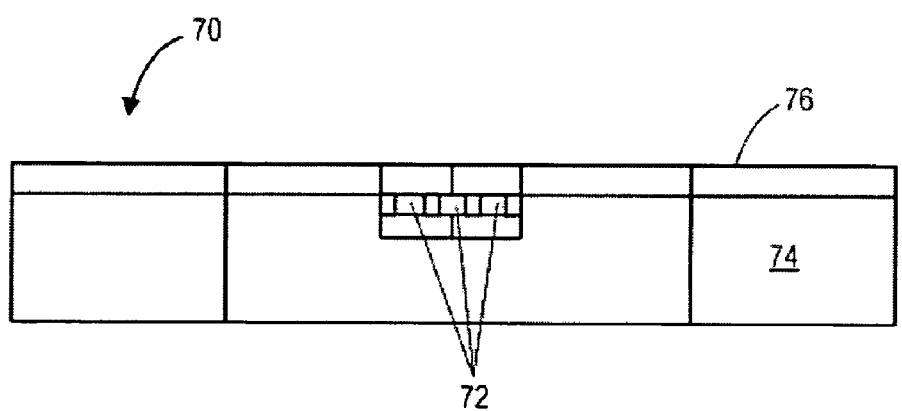

In yet another embodiment of the invention as shown in FIGS. 7A and 7B, a microfluidic chip 70 can be formed with a two-layer construction. The microfluidic chip 70 may include a polymer film layer 76 that encloses a series of one or more channels 72 formed in a bottom layer 74 as shown in FIG. 7A. A relatively open distal tip region 71 may protrude from the edge of the device 70 within the protected recessed area 73. The plurality of channels 72 formed in the bottom layer 74 of the chip 70 can extend up to the open distal tip region 71. Moreover, the recessed area 73 can be formed with a semi-circular configuration as illustrated or some other type of arcuate shape. The distal tip region 71 may be formed with a pointed tip 78 that is protected within the recessed area 73. FIG. 8B illustrates a side view of the microfluidic chip 70 formed with two polymer plates 74 and 76. Rather than selecting a separate thin polymer film to form the ESI tip, one of the two polymer plates may be monolithically configured to provide the tip. In the illustrated embodiment, the bottom polymer layer 74 is formed with three separate channels 72 leading up to the electrospray tip 78. A pair of relatively outer channels 72 may be selected to provide a sheath flow to assist the electrospray process, and the relatively inner channel may be designated for spraying a sample fluid and a calibration solution, respectively. Alternatively, as with other variations of the invention provided herein, the outer channels may be selected to introduce one or more additional sample fluids.

Another aspect of the invention provides methods of creating recessed edge-emitting electrospray tips using a thin film of metal-coated polymer bonded in between two polymer layers. For example, a readily manufacturable fabrication process may include the step of forming a tip that is placed within a semi-circular recess to protect it. The fabrication process may employ commercially available laser-cutting apparatus to form and shape a thin film of metal-coated polymer as desired thus avoiding photolithography and etching processes. These thin films can be cut in very rapid succession in a cost-effective manner by laser apparatus such as a frequency-tripled YAG laser. The cutting process may thus take only a few seconds which are needed to cut the pattern for a selected chip. The metal coating of the thin film polymer may serve as the electrical contact to the ESI tip. The separate manufacturing step for the ESI tip may be incorporated with the overall assembly process for the microfluidic chips provided herein.

Figure 8:
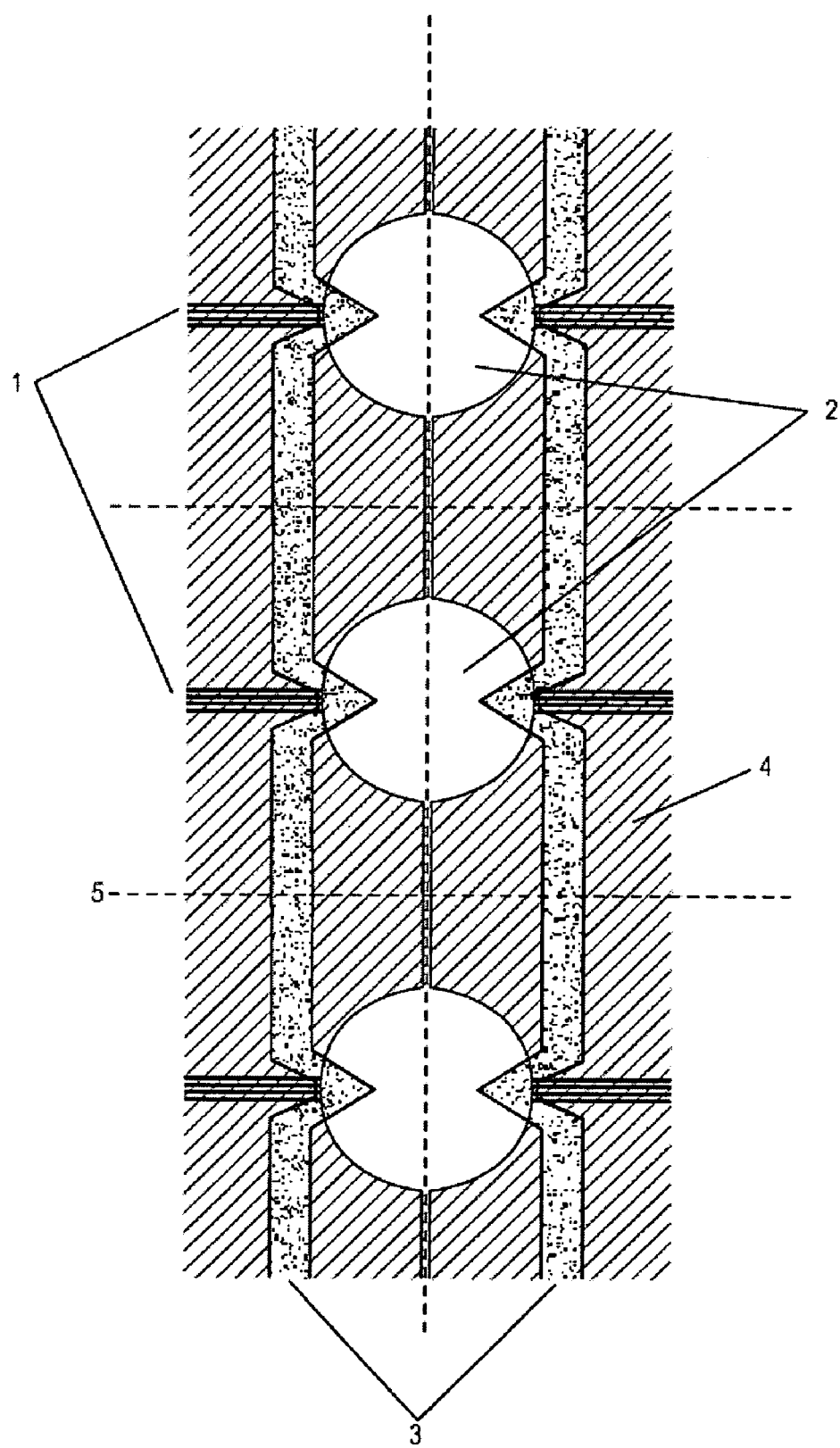
FIG. 8 is a diagram describing the manufacturing of microfluidic chips in batch quantities as provided by another aspect of the invention.

As shown in FIG. 8, a preferable method of manufacturing microfluidic chips in batch quantities is provided in accordance with another aspect of the invention. This method may be described as follows: (1) emboss the fluid channels for multiple microfluidic chips onto a polymer plate as described herein, including the formation of patterns at the edge of the chip for aligning two selected polymer plates; (2) drill a circular opening centered at the edge of each pair of adjacent chips along the polymer plates so that all of these openings can be drilled successively in the same operative step; (3) place a pre-formed strip of a laser-cut metal-coated polymer (see FIG. 6A) between the two plates that is aligned with the etched channel patterns—a single thin-film strip of a metal-coated polymer may be used for an entire row of adjacent chips on a plate; (4) thermally or otherwise bond the two polymer plates to seal the thin-film polymer (see FIG. 6B), preferably without distorting or flattening the cross-section of the embossed fluid channels; (5) separate the chips using CNC milling, sawing or die cutting techniques by forming cuts that go through the centers of the holes drilled earlier in Step (2). It shall be noted that these and other processes falling within the scope of the invention can be carried out on polymer plates which contain many chips. This can make chip fabrication cost-effective and substantially eliminate many of the time-consuming processes that are carried out on individual chips such as shaping the edges of each individual chip into a tip by machining processes. The microfluidic chips fabricated in accordance with this aspect of the invention offer many additional advantages over conventional devices that are embodied in a single microfluidic chip, including but not limited to following: (a) a tip that may be recessed and protected from mechanical damage; (b) a tip that may be metal-coated thus conveniently providing an electrical contact for electrospray ionization; (c) a plurality of fluid channels terminating at a single common ESI tip for emission of multiple fluids and samples; (d) etched alignment features that may be used to accurately align the thin polymer plates to form the microfluidic chips; and (e) a single laser-cut strip of metal-coated thin-film polymer used during a fabrication process that is sandwiched in between polymer plates for the production of entire rows of microfluidic chips.

While the invention has been described with reference to the aforementioned specification, the descriptions and illustrations of the preferable embodiments herein are not meant to be construed in a limiting sense. It shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art upon reference to the present disclosure. It is therefore contemplated that the appended claims shall also cover any such modifications, variations and equivalents.

What is claimed is:

1. A microfluidic chip for mass spectrometric analysis comprising:
    a microfluidic body layer formed with at least one fluid reservoir;
    at least one defined microchannel formed along the microfluidic body layer that is in fluid communication with the fluid reservoir; and
    a laminate layer for enclosing the defined microchannel formed along the microfluidic body layer, wherein the laminate layer extends beyond a tapered end portion of the microfluidic body layer to form a open-ended distal tip portion at which the defined microchannel terminates to provide an electrospray ionization tip that directs an ionization spray from the microfluidic chip.

2. The microfluidic chip as recited in claim 1, wherein at least a portion of the open-ended distal tip portion is covered with a hydrophilic material.

3. The microfluidic chip as recited in claim 1, wherein the tapered end portion of the microfluidic body layer is a two-dimensional taper formed along a relative X-Y axis and a relative Y-Z axis.

4. The microfluidic chip as recited in claim 1, wherein the tapered end portion of the microfluidic body layer includes a tapered end formed along a substantially flat truncated portion of the tapered end portion.

5. The microfluidic chip as recited in claim 4, wherein the tapered end has a thickness of less than 500 μm.

6. The microfluidic chip as recited in claim 1, wherein the microfluidic body layer includes an extended platform section having a flat tapered portion.

7. The microfluidic chip as recited in claim 6, wherein the flat tapered portion of the extended platform section has a thickness of less than 500 μm.

8. The microfluidic chip as recited in claim 1, wherein a plurality of microchannels are formed along the microfluidic body layer that are enclosed by the laminate layer to provide an electrospray ionization tip whereby each microchannel terminates to direct an ionization spray from the microfluidic chip.

9. The microfluidic chip as recited in claim 1, wherein the laminate layer is formed with a distal tip groove.

10. A microfluidic chip for electrospray ionization comprising:
    a channel plate formed with at least two non-intersecting fluid channels that are each in fluid communication with at least one fluid reservoir also included with the channel plate; and
    a covering plate for substantially enclosing the non-intersecting fluid channels formed on the channel plate, wherein the covering plate includes an overhang that extends beyond a tapered end portion of the channel plate to provide an electrospray tip that includes an open-tip region at which each of the non-intersecting fluid channels terminate.

11. The microfluidic chip as recited in claim 10, wherein the tapered end portion of the channel plate is dual-tapered and formed along two-dimensions defined by a relative X-Y axis and a relative Y-Z axis.

12. The microfluidic chip as recited in claim 10, wherein the electrospray tip is formed within a recessed portion of the microfluidic chip.

13. The microfluidic chip as recited in claim 12, wherein the electrospray tip is formed with a sharp point that is protected within the recessed portion of the microfluidic chip.

14. The microfluidic chip as recited in claim 10, wherein the covering plate is formed with a tip groove.

15. The microfluidic chip as recited in claim 10, wherein the channel plate and covering plate are formed of a material selected from at least one of the following: a polymer, a copolymer, an elastomer, a ceramic, quartz, silicon, silicon dioxide, silica, and glass.

16. The microfluidic chip as recited in claim 10, wherein the channel plate is defined with a first side and second opposite side separated along a longitudinal axis, and wherein at least one fluid channel is formed on the first side of the channel plate and at least one fluid channel is formed on the second opposite side of the channel plate.

17. A microfluidic chip for mass spectrometric analysis comprising:
    a body layer formed with a plurality of reservoirs for containing at least one fluid medium, wherein a plurality of separated channels are formed within the body layer that are each in fluid communication with at least one reservoir but not in fluid communication with each other within at least a portion of the body layer; and
    an enclosure layer for enclosing at least a portion of the separated channels formed within the body layer, wherein the enclosure layer further includes an exposed open-tip extension extending beyond a dual-tapered end portion of the body layer to provide an electrospray ionization tip at which the plurality of separated channels terminate to direct an ionization spray from the microfluidic chip.

18. The microfluidic chip as recited in claim 17, wherein the exposed open-tip extension and the enclosure layer are formed as a single-piece to provide a monolithic electrospray tip.

19. The microfluidic chip as recited in claim 17, wherein the exposed open-tip extension and the enclosure layer are separate pieces that are joined together.

20. The microfluidic chip as recited in claim 17, wherein the exposed open-tip extension is formed with a groove tip.

21. A microfluidic chip with enhanced electrospray tip for mass spectrometric analysis comprising:
    a microfluidic chip formed with at least one fluid reservoir for containing at least one fluid medium;
    at least one microchannel channel formed within the microfluidic chip that is in fluid communication with the fluid reservoir; and
    an electrospray ionization tip formed with a tapered open-ended distal tip portion positioned along an end surface of the microfluidic chip, wherein the microchannel terminates at the open-ended distal tip portion to direct an ionization spray from the microfluidic chip.

* * * * *